United States Patent
Ferro et al.

(10) Patent No.: US 10,751,037 B2
(45) Date of Patent: *Aug. 25, 2020

(54) SURGICAL RETRACTOR

(71) Applicant: AOD Holdings, LLC, Arroyo Grande, CA (US)

(72) Inventors: Thomas D. Ferro, Arroyo Grande, CA (US); Donald J. Lee, San Luis Obispo, CA (US); Joseph Phillips, Paso Robles, CA (US); Christiana M. Ferro, San Luis Obispo, CA (US); Austin T. Ferro, Arroyo Grande, CA (US); Scott C. Gill, San Luis Obispo, CA (US)

(73) Assignee: AOD Holdings, LLC, Arroyo Grande, CA (US)

(*) Notice: Subject to any disclaimer, the term of this patent is extended or adjusted under 35 U.S.C. 154(b) by 41 days.

This patent is subject to a terminal disclaimer.

(21) Appl. No.: 15/996,467

(22) Filed: Jun. 2, 2018

(65) Prior Publication Data

US 2018/0280011 A1    Oct. 4, 2018

Related U.S. Application Data

(63) Continuation of application No. 14/861,907, filed on Sep. 22, 2015, now Pat. No. 9,986,988.

(60) Provisional application No. 62/085,309, filed on Nov. 27, 2014.

(51) Int. Cl.
*A61B 17/02* (2006.01)
*A61B 17/00* (2006.01)
*A61B 90/00* (2016.01)

(52) U.S. Cl.
CPC .... *A61B 17/02* (2013.01); *A61B 2017/00473* (2013.01); *A61B 2017/00858* (2013.01); *A61B 2090/0801* (2016.02)

(58) Field of Classification Search
CPC ... A61B 17/02; A61B 17/0218; A61B 17/025; A61B 17/0281; A61B 2017/0212; A61B 2090/0801
See application file for complete search history.

(56) References Cited

U.S. PATENT DOCUMENTS

| 3,068,869 A | * | 12/1962 | Shelden et al. | A61B 17/08 606/216 |
| 5,483,760 A | * | 1/1996 | Kataoka | A43B 5/06 36/129 |
| 5,716,358 A | * | 2/1998 | Ochoa | A61B 17/68 606/301 |

(Continued)

FOREIGN PATENT DOCUMENTS

WO    2013188684    12/2013

*Primary Examiner* — Ellen C Hammond
(74) *Attorney, Agent, or Firm* — McDonnell Boehnen Hulbert & Berghoff LLP

(57) ABSTRACT

A surgical retractor and configured to minimize tearing of the gloves without compromising the ability to grip tissue. The surgical retractor has a handle, a blade, and a plurality of retraction elements. The retraction elements may be fixed to the blade but arranged in a specific configuration that minimizes tearing of the gloves without compromising the ability to grip tissue. The retraction elements may also be made deployable by having a deployed configuration in which the retraction elements are exposed, and a stowed configuration in which the retraction elements are hidden.

21 Claims, 18 Drawing Sheets

(56) References Cited

U.S. PATENT DOCUMENTS

| | | | |
|---|---|---|---|
| 6,334,856 B1 | 1/2002 | Allen et al. | |
| 6,394,951 B1 | 5/2002 | Taylor et al. | |
| 6,743,169 B1 | 6/2004 | Taylor et al. | |
| 6,821,281 B2 | 11/2004 | Sherman et al. | |
| 7,056,287 B2 | 6/2006 | Taylor et al. | |
| 7,131,987 B2 * | 11/2006 | Sherman | A45D 26/0004 604/290 |
| 7,507,202 B2 | 3/2009 | Schoellihorn | |
| 7,585,277 B2 | 9/2009 | Taylor et al. | |
| 7,828,827 B2 * | 11/2010 | Gartstein | A45D 26/0004 606/290 |
| 8,075,826 B2 | 12/2011 | Lastovich et al. | |
| 8,273,102 B2 * | 9/2012 | Danitz | A61B 17/122 606/207 |
| 8,277,476 B2 | 10/2012 | Taylor et al. | |
| 8,702,726 B2 | 4/2014 | Garstein et al. | |
| 8,708,966 B2 | 4/2014 | Allen et al. | |
| 8,865,288 B2 | 10/2014 | Bhandari et al. | |
| 9,986,988 B2 * | 6/2018 | Ferro | A61B 17/02 |
| 2008/0086034 A1 * | 4/2008 | Schmitz | A61B 17/00234 600/210 |
| 2009/0192360 A1 * | 7/2009 | Riess | A61B 17/02 600/210 |
| 2013/0040261 A1 * | 2/2013 | Kwon | A61C 3/03 433/102 |
| 2013/0172915 A1 | 7/2013 | Thomas et al. | |
| 2014/0257039 A1 * | 9/2014 | Feldman | A61B 17/02 600/205 |
| 2014/0323811 A1 * | 10/2014 | DeSantis | A61B 1/06 600/213 |
| 2016/0015467 A1 * | 1/2016 | Vayser | G06N 5/02 600/245 |

\* cited by examiner

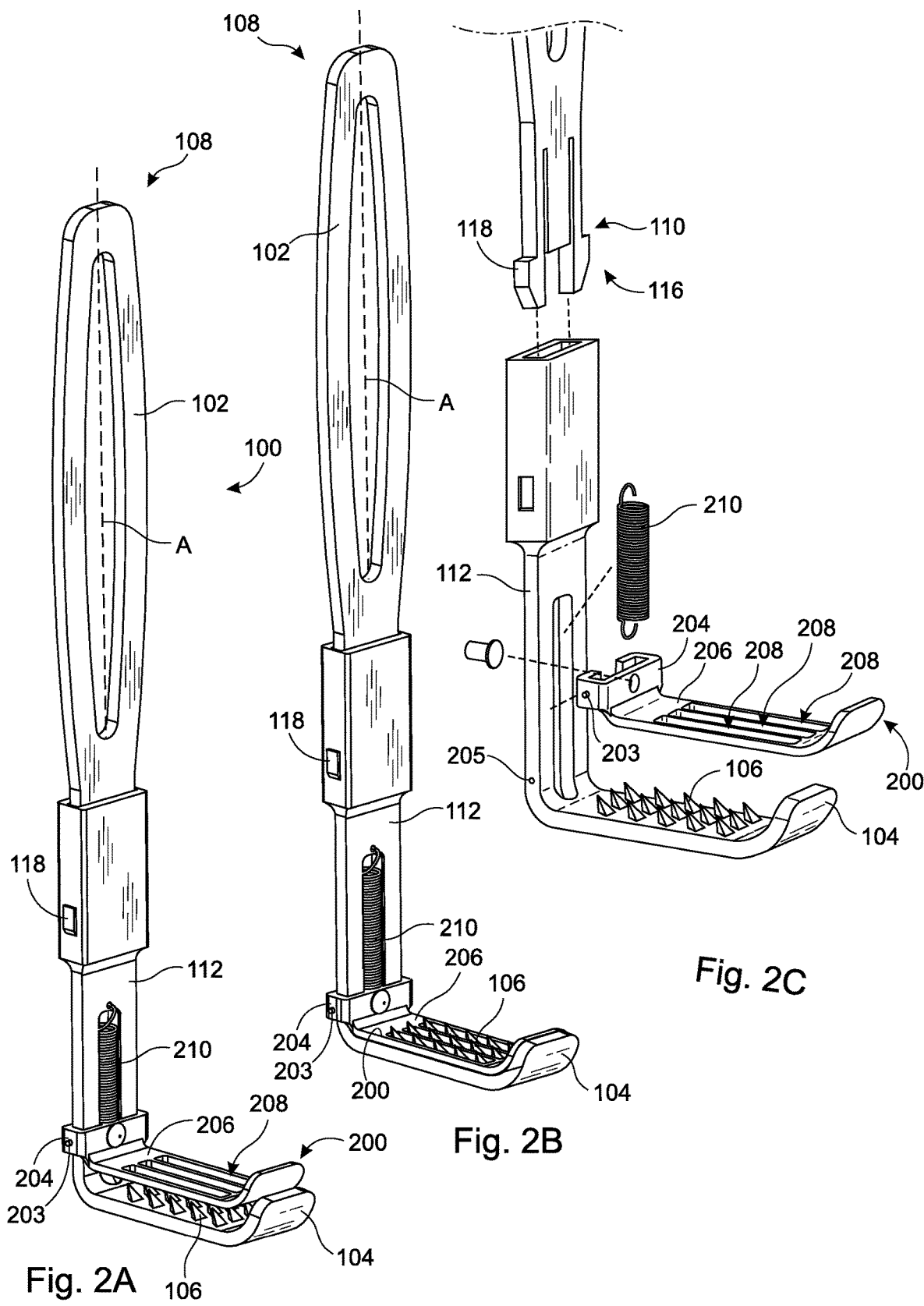

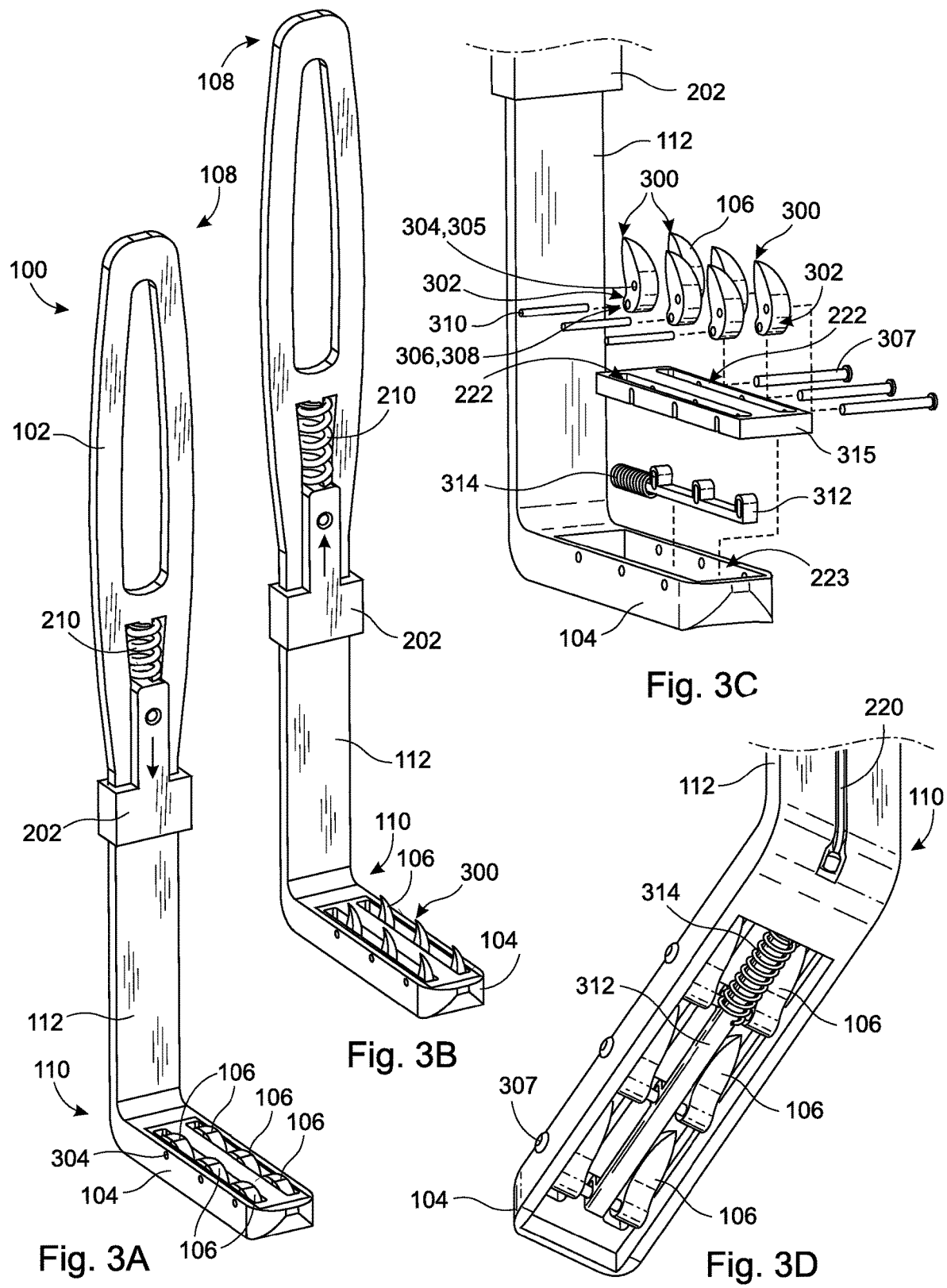

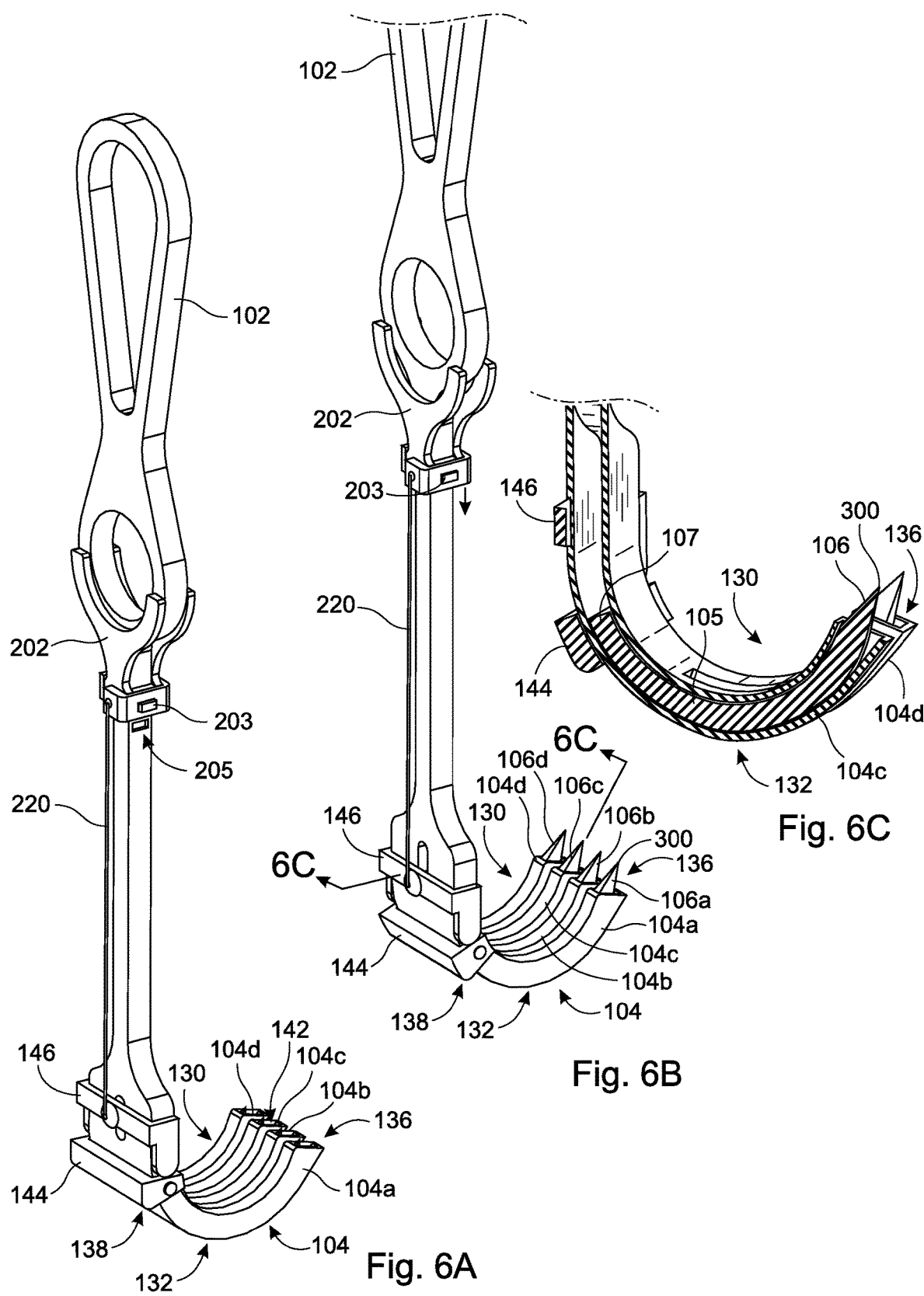

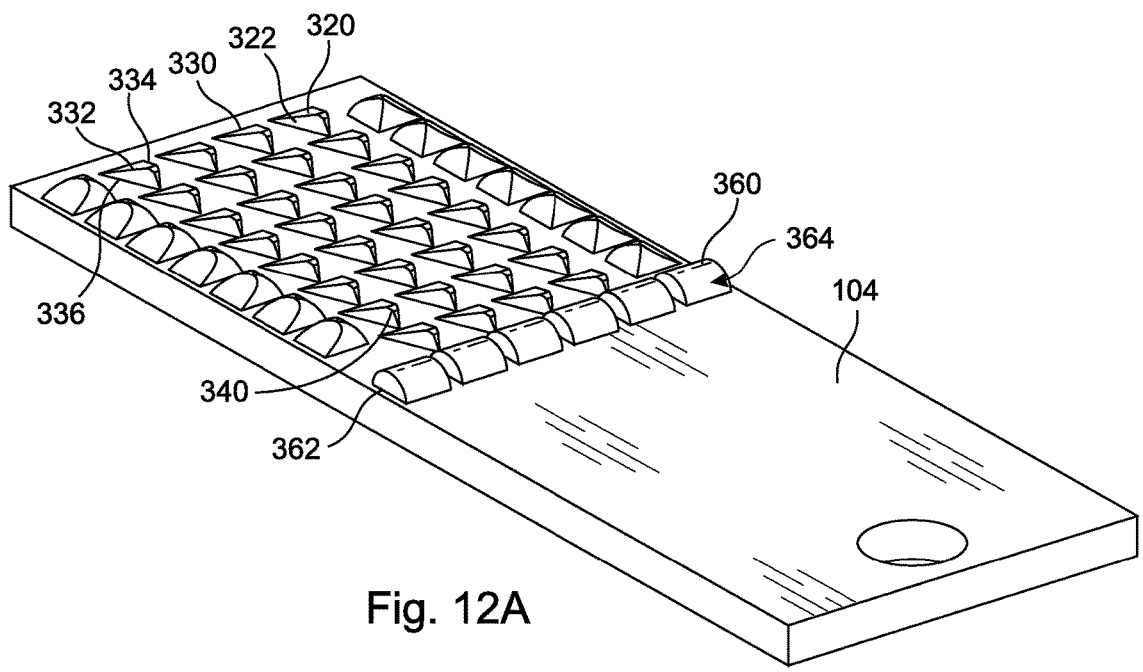
Fig. 12A
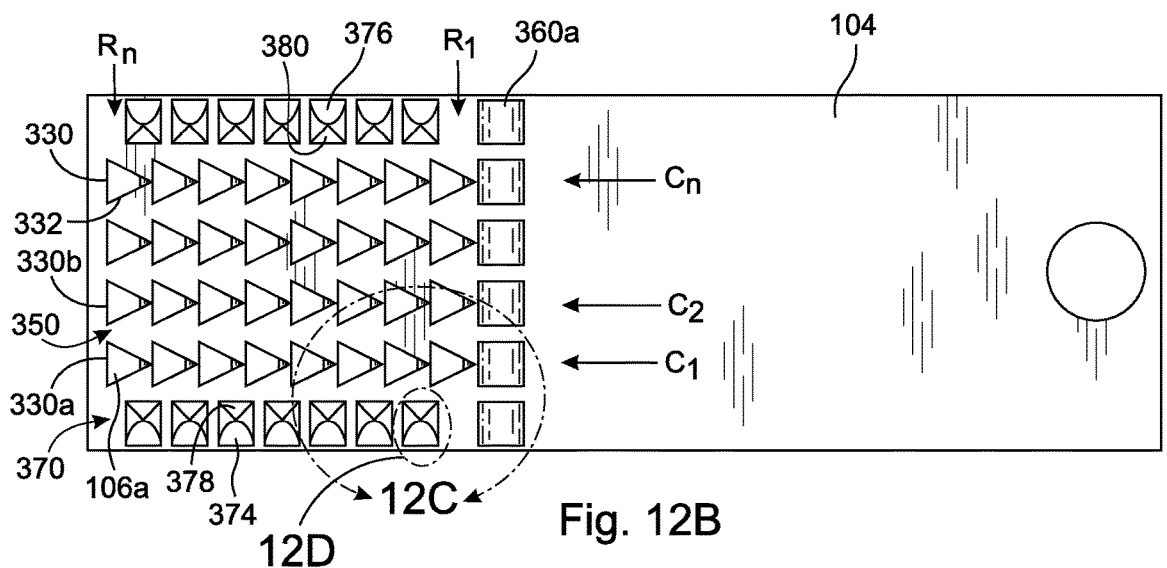
Fig. 12B
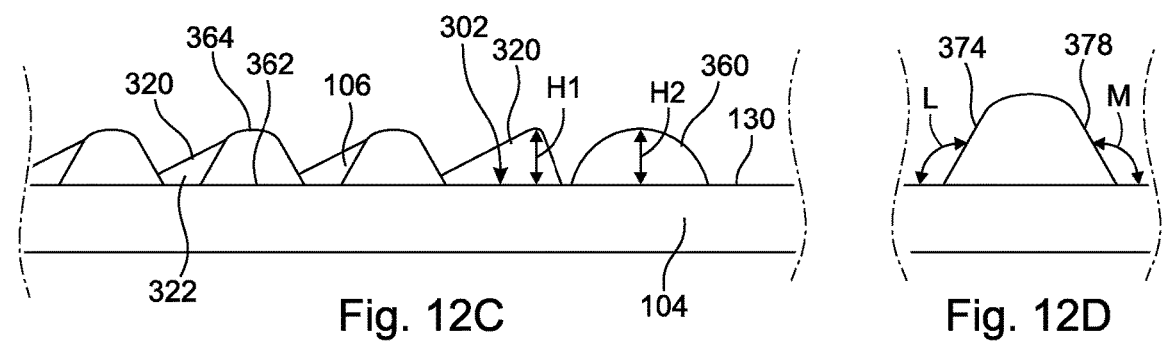
Fig. 12C
Fig. 12D

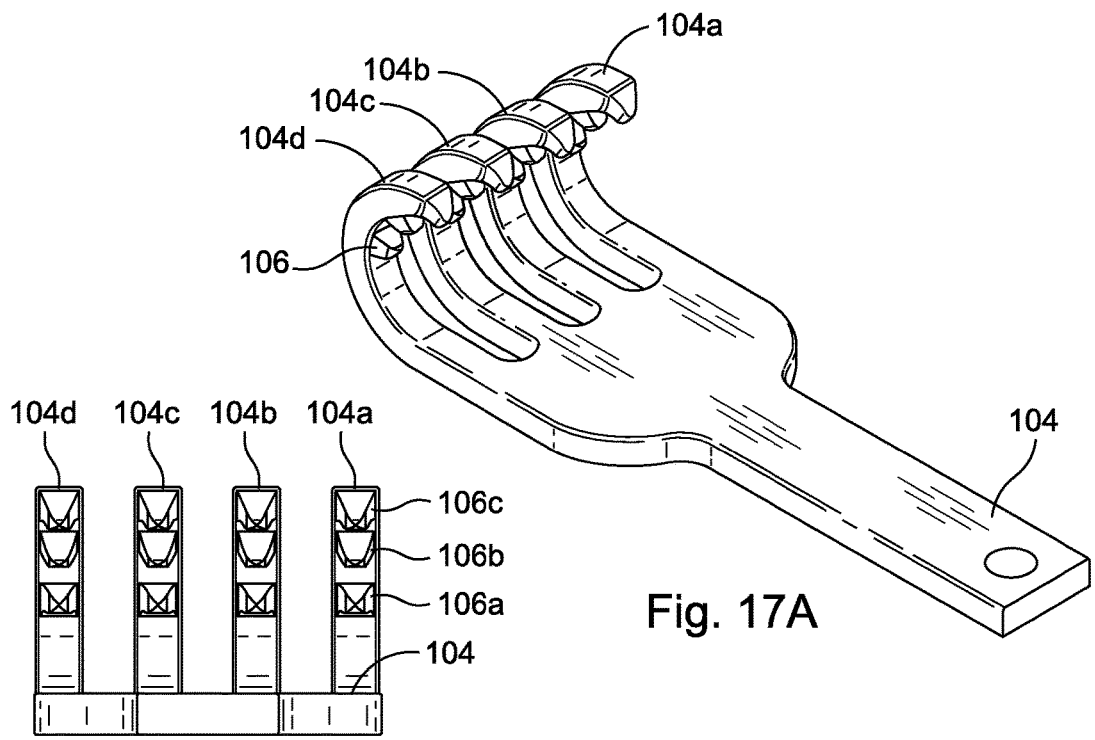
Fig. 17A
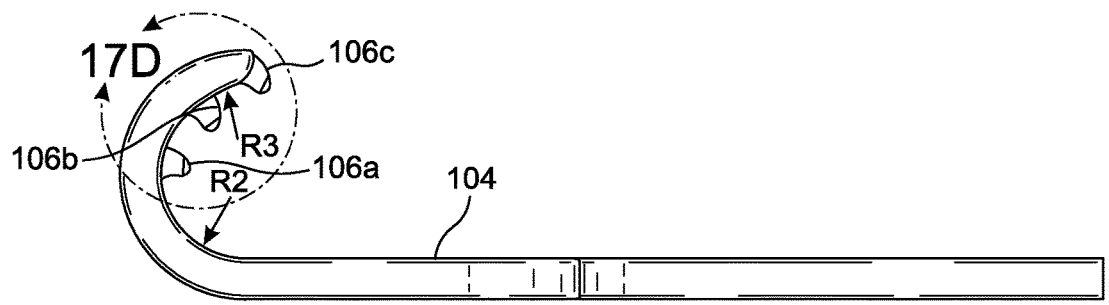
Fig. 17B
Fig. 17C
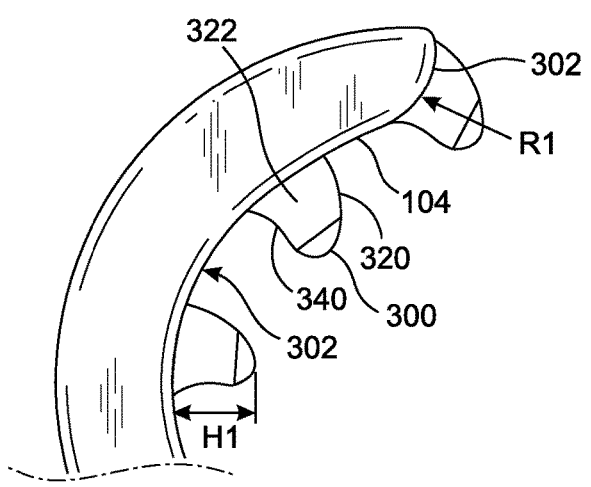
Fig. 17D

SURGICAL RETRACTOR

CROSS REFERENCE TO RELATED APPLICATIONS

The present application is continuation application of U.S. patent application Ser. No. 14/861,907 filed Sep. 22, 2015 which claims priority to U.S. Provisional Patent Application Ser. No. 62/085,309 filed Nov. 27, 2014. The entire disclosure contents of these applications are herewith incorporated by reference into the present application.

TECHNICAL FIELD

This invention relates to surgical retractors.

BACKGROUND

Surgical retractors are bent or flat metal instruments that are used to manipulate a surgical incision that has been made in a patient. The retractor is typically placed upon the incision's edges, and leverage or pulling force is applied to hold the incision open or otherwise moved around to allow the user better access to the site of operation.

Users of the retractor may hold the retractor in place with their hands, or clamp the retractor locally. A robotic arm may also hold the retractor in position as well.

Retractors come in different sizes, shapes, and are usually made from the 300 or 400 series of stainless steel. The steel can be formed into a retractor by progressive die stamping, or other forms of metalworking that can produce a curved shape in two axes. Metal retractors are designed for a long service life and many rounds of sterilization.

Depending on the type of retractors and the intended use, the retractors may be equipped with teeth or retraction elements to better grip tissue. Although the teeth enhance the gripping feature, the teeth also pose a danger to puncturing the surgical gloves worn by the surgeon or other health care providers that might be assisting the surgeon. Punctured gloves can lead to health hazards for both the healthcare provider and patient.

Therefore, there is still a need for improved surgical retractor with enhanced tissue gripping capability but also minimizes the threat of inadvertently puncturing gloves or excessively tearing the tissue.

SUMMARY

The present invention is directed towards surgical retractors that provide enhanced gripping capabilities on the tissue while minimizing the inadvertent puncturing or tearing of surgical gloves during use. In some embodiments, the retraction elements may be made deployable so that in use the retraction elements are exposed, but when not in use, the retraction elements are in a stowed or hidden configuration. In some deployable embodiments, a guard may be applied to the retraction elements to expose or hide the retraction elements. In other deployable embodiments, the retraction elements themselves may move into a deployed or stowed configuration. In some embodiments, the two techniques may be combined.

In some embodiments, the surface of surgical retractors that come in contact with the soft tissue of the patient during surgery are configured to minimize tearing or puncturing of gloves without compromising the gripping capabilities. The invention applies a texture to the surface that comes in contact with the soft tissue to reduce the possibility of slipping and losing grip of the soft tissue. The increased grip will reduce the necessity for excessive force to hold the incision open and will reduce blunt force trauma that may damage the soft tissue.

The texture that is applied to the surface of the retractors is designed not to cause any harm to the user or damage any protective outerwear such as the gloves. This can be achieved by creating a tightly meshed anisotropic pattern of structures that will texture the retractor surface. The features that make up the texture may be, but is not limited to, sharp anisotropic structures that are spaced closely to distribute the stress points that occur when the textured surfaces engage soft tissue, or any other conforming material.

The texture may be designed to be injection molded into plastic retractor bodies as well as traditional metal ones. The plastic retractor bodies may be single-use, disposable surgical retractors. This will decrease costs by eliminating repeated sterilization.

When these textures are applied to traditional "smooth" retractors, these surfaces open up new opportunities for retraction efficiencies and possibilities for smaller "minimally invasive" surgical approaches, and increased surgeon efficiency in the operating room.

BRIEF DESCRIPTION OF DRAWINGS

FIG. 2A-2C show perspective views of an embodiment of a deployable surgical retractor in the stowed configuration, deployed configuration, and exploded, respectively.

FIGS. 3A-3D show perspective views of another embodiment of a deployable surgical retractor in the stowed configuration, deployed configuration, exploded, and from the bottom, respectively.

FIGS. 6A-6B show perspective views of another embodiment of a deployable surgical retractor in the stowed configuration and the deployed configuration, respectively.

FIG. 6C shows a side cross-sectional view taken through line 6C-6C of FIG. 6B.

FIGS. 12A-12D show a perspective view, a top view, a close-up side view taken of 12C shown in FIG. 12B, and a close-up front view of 12D shown in FIG. 12B, respectively, of another embodiment of a retraction surface with fixed retraction elements.

FIG. 17A shows an embodiment of the retraction elements from FIG. 16A as applied to a Volkman-type surgical retractor.

FIG. 17B is a top view of the embodiment in FIG. 17A.
FIG. 17C is a side view of the embodiment in FIG. 17A.
FIG. 17D is a close-up of the area indicated as 17D in FIG. 17C.

DETAILED DESCRIPTION OF THE INVENTION

Figure 1A:
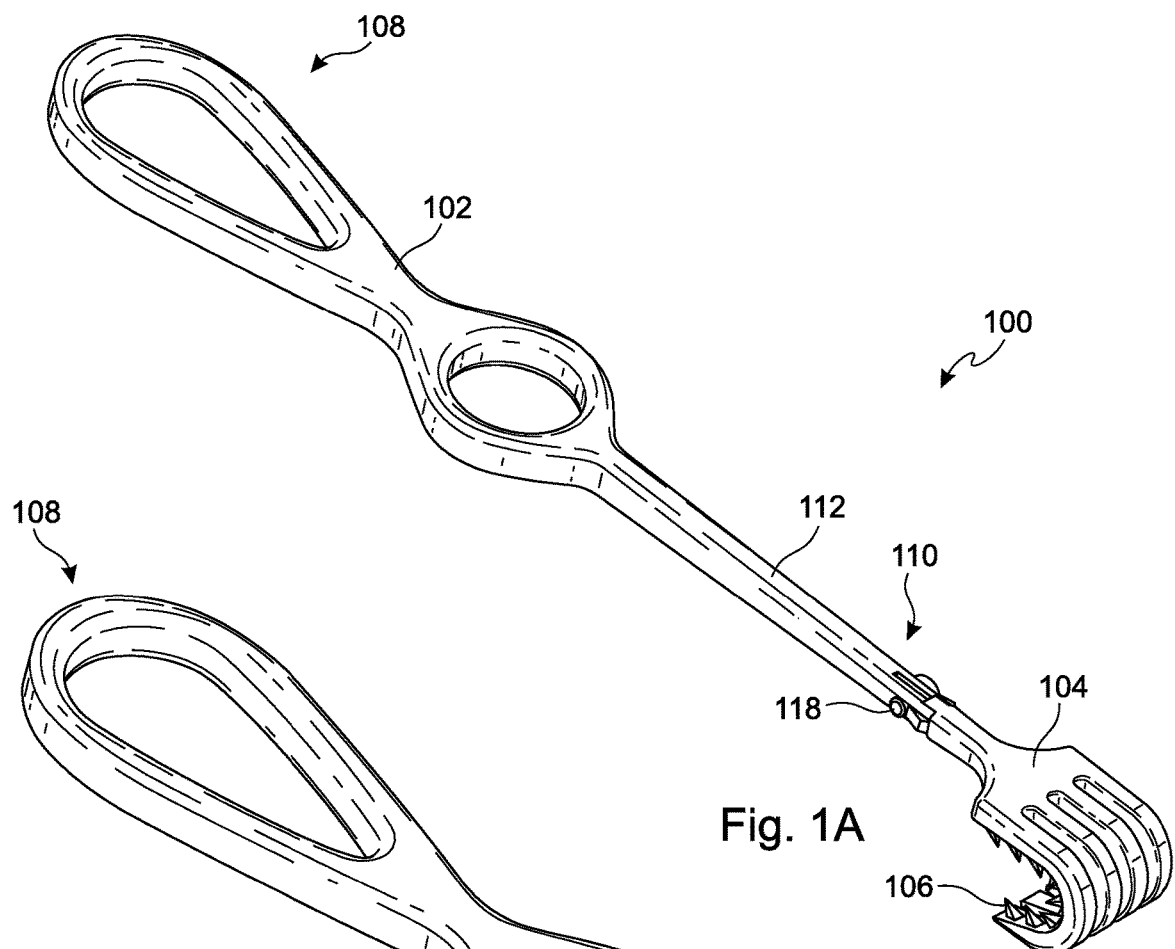
FIGS. 1A-1B show perspective views of a surgical retractor assembled and with the blade removed, respectively.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The surgical retractor 100 of the present application is an improvement over traditional retractors in that the retractor 100 of the present application is configured to minimize or reduce the chances of surgical gloves being inadvertently torn by the retraction elements 106 without compromising the gripping action on the tissue by the retraction elements 106. For example, in some embodiments, the retraction elements may be deployable (e.g., FIGS. 2A-7B). In some embodiments, the retraction elements 106 may be fixed but have a strategic configuration and/or arrangement (e.g., FIGS. 8A-18D).

With reference to the figures, in general, the surgical retractor 100 of the present application comprises a handle 102, a blade 104 and a neck region 112 operatively connecting the handle 102 to the blade 104. The handle 102 is located at a distal end 108 of the surgical retractor 100, and the neck 112 is located at a proximal end 110. The blade 104 is operatively connected to the neck 112 at the proximal end 110, meaning that the blade may be attached to the neck 112, detachably attached to the neck 112, or integrally formed with the neck 112 as a single integrally formed unit. The retractor 100 may be constructed of stainless steel. In some embodiments, the retractor 100 may be made of plastic so as to be disposable. Other standard material can be used. The blade 104 comprises a plurality of retraction elements 106, also referred to as teeth, projecting from a top surface 130 of the blade 104. The retraction elements 106 may be configured to minimize tearing or puncturing of a glove during use, without compromising the gripping action against tissue.

Figure 1B:
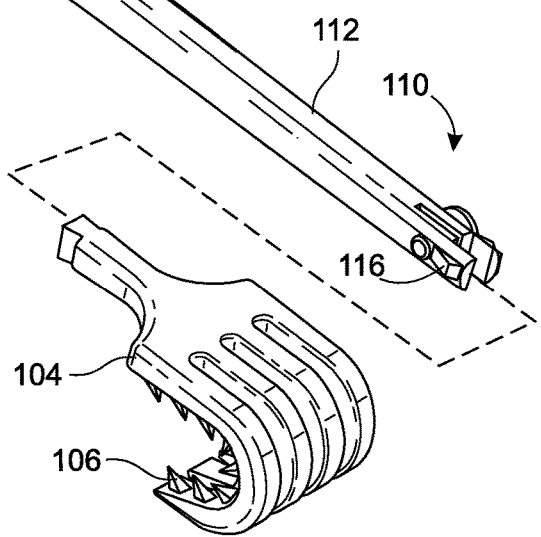

In some embodiments, as shown in FIGS. 1A and 1B, the blade 104 may be removable (i.e. detachable) from the neck 112 so that the blade 104 can be replaced with another blade. Having interchangeable blades 104 allows the user (i.e. surgeon, nurse, physician's assistant, interns, any other healthcare professional, and the like) to replace a damaged blade, or provides the user with a variety of types of retraction elements 106 for specific uses. The blade 104 can be made removable from the handle 102 by a locking device 116. The blade 104 may comprise an orifice that can slide over the neck of the retractor 100 at the proximal end 110. As the blade slides over the neck 112, the locking device 116 locks onto a notch inside the blade 104. The locking device 116 comprises a release button 118 that, when pressed, causes the locking device 116 to release the blade 104 from the handle 102. This and other types of locking devices 116 can be used for any of the embodiments described herein.

Some embodiments utilize deployable retraction elements to minimize tearing of gloves without compromising gripping action. Deployable retraction elements means that the retraction elements 106 can be exposed for use or hidden from use so that they cannot get caught on any item inadvertently, such as surgical gloves. Deployment of the retraction elements 106 can occur by moving the retraction elements 106 themselves, or by moving a guard 200 relative to the retraction elements 106 to expose or hide the retraction elements 106.

With reference to FIGS. 2A-2C, one type of deployable surgical retractor has a guard 200 slidably mounted on the neck 112 of the surgical retractor 100. FIG. 2A shows a perspective view of a stowed configuration in which the guard 200 hides the retraction elements 106 from being exposed. FIG. 2B shows a perspective view of the retractor 100 in FIG. 2A in a deployed configuration in which the retraction elements 106 are exposed. FIG. 2C shows an exploded perspective view of the embodiments shown in FIGS. 2A and 2B.

The handle 102 defines a longitudinal axis A. The guard 200 is mounted directly above the retraction elements 106 perpendicular to the longitudinal axis A and in a manner that allows the guard 200 to slide up and down along the longitudinal axis A on the neck 112.

For example, the guard 200 may comprise a slide bracket 204 and a plate 206 attached to the slide bracket 204. The plate 206 has a plurality of openings 208 through which the retraction elements 106 can pass. The slide bracket 204 is slidably mounted on the neck 112. In the preferred embodiment, the slide bracket 204 is biased away from the blade 104. For example, the slide bracket 204 may be operatively connected to one end of a spring 210. The opposite end of the spring 210 is fixed on the neck 112. The spring 210 imposes a biasing force on the slide bracket 204 to pull the slide bracket 204 towards the distal end 108 of the retractor 100 and away from the blade 104. Similarly, a spring 210 can be positioned to push the slide bracket 204 towards the distal end 108.

The plate 206 is configured to mate or spoon with the blade 104. Therefore, from a side profile view, the plate 206 may resemble the blade 104. The thickness of the plate 206 is less than the height of the retraction elements 106. When the guard 200 is properly mounted on the neck 112, each opening 208 of the plate 206 aligns with one or more retraction element 106. In some embodiment, each retraction element 106 may have a separate and independent corresponding opening 208 on the plate 206. In some embodiments, where the retraction elements 106 are aligned in columns, the openings 208 may comprise a plurality of slits, wherein one slit is configured to correspond with one column of retraction elements 106.

In use, the spring 210 causes the guard to naturally move away from the blade 104. Therefore, the guard 200 hovers above the blade 104. The guard 200 is high enough above the blade 104 so that the retraction elements 106 cannot protrude past the guard 200. At the same time, the guard 200 is close enough to the retraction elements 106 so that unwanted items are not caught in the retraction elements 106 from underneath the guard 200. Therefore, when not in use, the retraction elements 106 are hidden from use or in the stowed configuration, and the surgical retractor 100 is safe for handling.

To expose or deploy the retraction elements 106, the user uses the surgical retractor 100 just like any typical retractor by placing the top surface 130 of the blade 104 against the tissue to be retracted and pulling on the handle 102. With the present embodiment, however, when the surgical retractor 100 is applied to the tissue, the guard 200 is the first to contact the tissue. Pulling on the handle 102 imposes a biasing force against the guard 200, thereby overriding the spring 210, which causes the guard 200 to move towards the blade 104. Eventually, with sufficient force the guard 200 is pushed against the top surface 130 of the blade 104 causing the blade 104 to mate or spoon with the guard 200 as the retraction elements 106 pass through their respective openings 208. Once the retraction elements 106 pass through the openings 208, the retraction elements 106 become exposed (the deployed configuration) allowing the retraction elements 106 to catch the tissue. When the user is finished, simply removing the surgical retractor 100 from the tissue will cause the spring 210 to move the guard 200 back into its natural position (the stowed configuration), thereby hiding the retraction elements 106.

In some embodiments, a locking mechanism 203, 205 such as that shown in FIGS. 6A and 6B, may be provided to lock the guard 200 in place in the deployed configuration. This, and other types of locking mechanisms, can be employed for any deployable surgical retractors 100 discussed herein. A release button may also be provided to release the guard 200 from its locked position. When the user has completed the use of the surgical retractor 100, the lock 203 can be disengaged from its catch 205, such as an orifice, hook, and the like, causing the spring 210 to move the guard 200 away from the blade 104 and hide the retraction elements 106. In some embodiments, the retraction elements 106 may naturally be in the stowed configuration, and deployed only when the retraction elements 106 are in use, and automatically stowed when not in use. In some embodiments, an actuator 202, as discussed below, may be provided to move the guard 200.

The embodiment in FIGS. 2A-2C also show the blade 104 detachable from the handle 102 via the locking device 116 and release button 118. The embodiment shown has the neck 112 detachable from the handle; however, this concept can be applied to have the blade 104 removable from the neck 112. The detachable concept can be applied to any embodiment described herein.

In embodiments with a lock 203 for the guard 200, the user can move the slide bracket 204 to the locked configuration to lock the plate 206 in the deployed configuration to expose the retraction elements 106. The surgical retractor 100 is then used like typical retractors. When finished, the guard 200 is released to hide the retraction elements 106.

In some embodiments, rather than using a guard 200 that hides or exposes the retraction elements 106, the retraction elements 106 themselves may be moveable into a deployed configuration in which the retraction elements 106 are exposed, and a stowed configuration in which the retraction elements 106 are hidden. In some embodiments, the surgical retractor 100 may have an actuator 202 wherein actuation of the actuator 202 exposes or hides the retraction elements 106. The actuator 202 may be positioned on the handle 102 so as to be convenient for the user to deploy or hide the retraction elements 106 with one hand.

For example, as shown in FIGS. 3A-3D, an actuator 202 is operatively connected to the retraction elements 106 so that movement of the actuator 202 causes the retraction elements 106 to deploy or be stowed. The actuator 202 may be operatively connected to the retraction elements 106 by a connecting element 220, such as a rod, cable, and the like. A spring 210 may connect the actuator 202 to the handle 102 creating a biasing force against the actuator 202. The biasing force against the actuator 202 causes the retraction elements 106 to maintain a stowed configuration so that the retraction elements are hidden from use as shown in FIG. 3A. For example, the retraction elements 106 may be rotated so that the tips 300 are embedded into the blade 104. To that effect, the blade 104 may have an opening, such as slots 222 or a cavity 223, inside which the retraction elements 106 reside. The retraction elements 106 can then be deployed from and stowed within the slots 222 or cavity 223.

As shown in the exploded view in FIG. 3C, each retraction element 106 comprises a tip 300 that catches the tissue, and a base 302 that connects the retraction element 106 to the blade 104. In this embodiment, the retraction elements 106 have a pivot point 304 in between the tip 300 and the base 302. The pivot point 304 may be a hole 305 through the retraction element 106 with a rod 307 inserted there through and fixed to the blade 104. At the base 302 is a connection point 306 to connect the base 302 to the connecting element 220. In the preferred embodiment, the connection point 306 comprises a hole 308 through the base 302, and a rod 310 is inserted into the hole 308. The rod 310 may be mounted on a shaft 312. The connecting element 220 is operatively attached to the retraction elements 106 through the shaft 312. A guide plate 315 is provided to fit within the cavity 223 of the blade 104 and guide the movement of the shaft 312.

Movement of the connecting element 220 causes the movement of the shaft 312. In this example, movement of the actuator 202 towards the distal end 108 of the retractor 100 causes the connecting element 220 to move towards the distal end 108. Due to the perpendicular arrangement of the connecting element 220 relative to the shaft 312, the shaft 312 moves towards the proximal end 110 of the retractor 100. This action causes the base 302 of the retraction element 106 to move towards the proximal end 110. Since the rod 307 of the pivot point is fixed to the blade 104, the retraction element 106 rotates about the rod 307 so as to perform an unfolding action. Due to the spring action causing the actuator 202 to move towards the proximal end 110 of the retractor 100, the retraction element 106 has a tendency to fold to the stowed configuration. In some embodiments, a second spring 314 may be attached to the shaft 312 to cause the shaft 312 to move away from the proximal end 110 causing the retraction elements 106 to fold into the stowed configuration. In some embodiments, spring 314 may be the only spring used. In some embodiments, both springs 210, 314 may be used.

Therefore, in use, the user uses the actuator 202 to deploy the retraction elements 106. Once deployed, the user can apply the surgical retractor 100 to the tissue. When the user releases the actuator 202, the retraction elements 106 tends towards the stowed configuration thereby catching the tissue. In some embodiments, the actuator 202 may be configured to lock the retraction elements 106 in the exposed (deployed) or hidden (stowed) configuration.

Figure 4A:
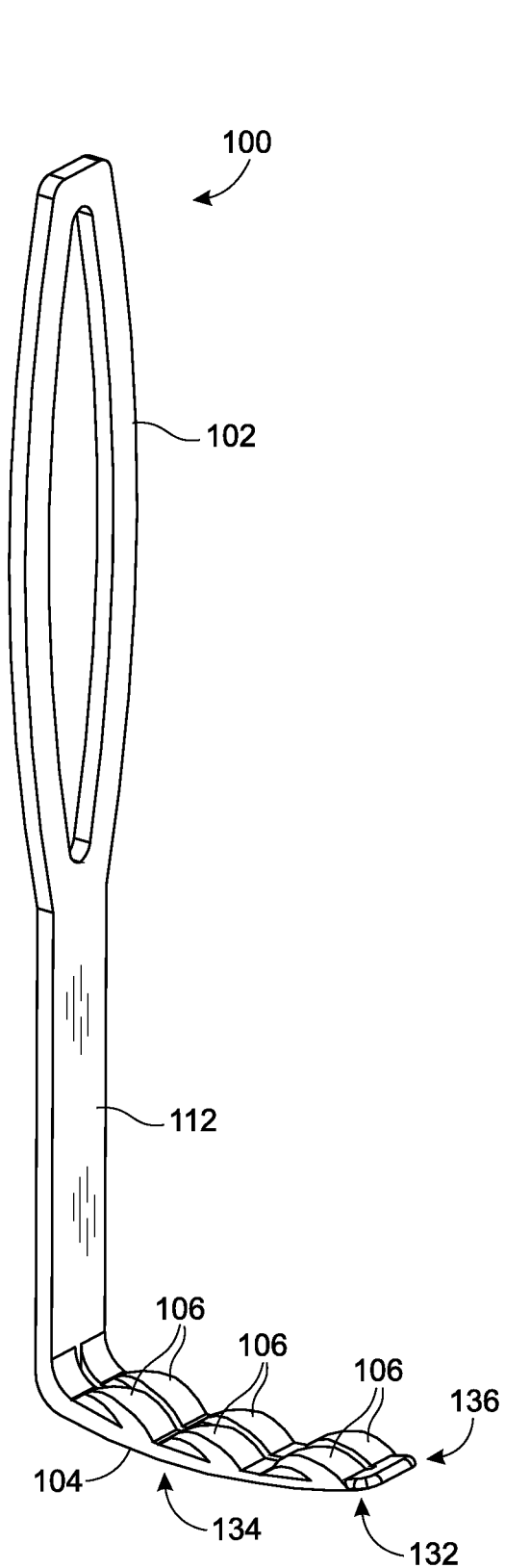
FIGS. 4A-4B show perspective views of another embodiment of a deployable surgical retractor in the stowed configuration and deployed configuration, respectively.
Figure 4B:
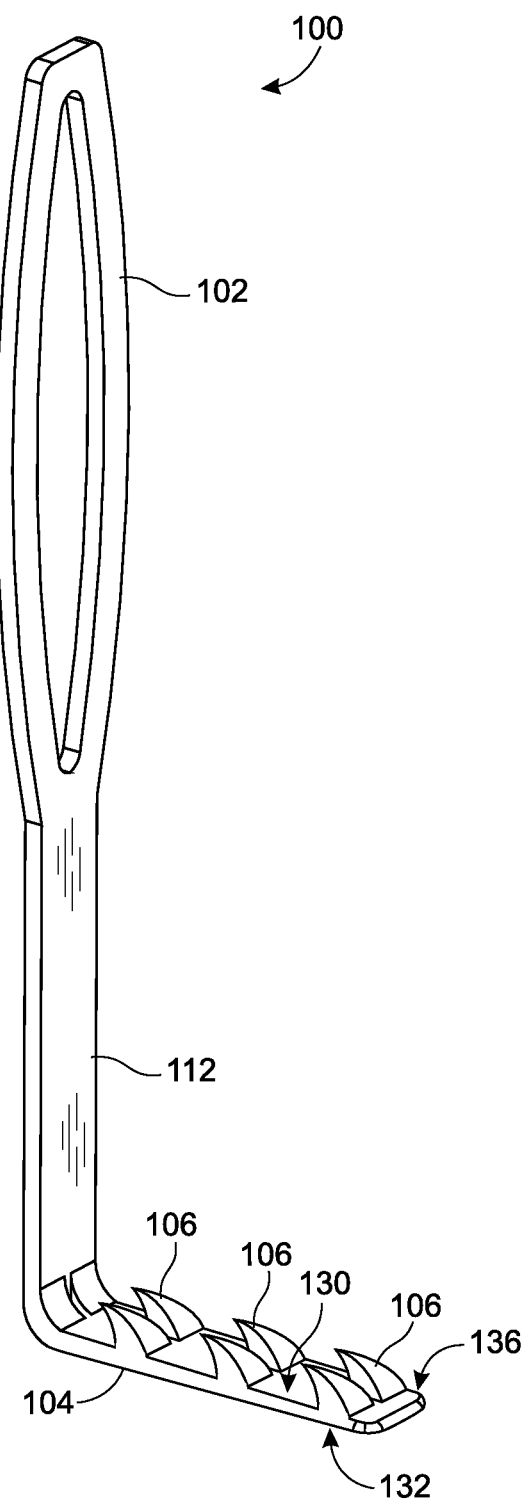

In some embodiments, as shown in FIGS. 4A-4B, the blade 104 may be flexible such that flexion of the blade 104 causes the retraction elements 106 to deploy. Therefore, the blade 104 and the retraction elements 106 may be integrally formed as a single unit. In addition, the blade 104 may be integrally formed with the handle 102. The blade 104 comprises a top surface 130 and a bottom surface 132 opposite the top surface 130. The retraction elements 106 may be located on the top surface 130 of the blade 104. The blade 104 is constructed to have two different configurations. In the first configuration, the top surface 130 of the blade 104 may have a concave shape as shown in FIG. 4A. In this configuration, the retraction elements 106 are in the stowed configuration in which the tips 300 of the retraction elements 106 are bent towards the top surface 130 so as to be hidden from use.

In a second configuration, force can be applied approximately to the center 134 of the bottom surface 132 or the free end 136 of the top surface 130 so as to force the top surface 130 to become flat or even convex as shown in FIG. 4B. This configuration is referred to as the deployed configuration and the tips 300 of the retraction elements 106 are exposed so as to be able to catch tissue. In some embodiments, once the blade 104 becomes flat or convex, the blade 104 may stay in that configuration until the blade 104 is manually bent back to the stowed configuration. In some embodiments, the blade 104 may always be biased towards its stowed configuration.

In use, when the retractor 100 is first making contact with the tissue, the free end 136 of the blade 104 would first make contact with the tissue, then the user would pull away from the incision in a radial direction. That motion would allow the clearance needed to expose the retraction elements 106 to engage with the tissue. In addition, the pull force is not solely horizontal, but at a slight upward angle which would allow the retraction elements 106 to remain exposed and engaged with the tissue. Alternatively, the user can apply a downward force at the free end 136 and an upward force against the center 134 to cause the retraction elements 106 to pop open for use.

Figures 5A, 5B:
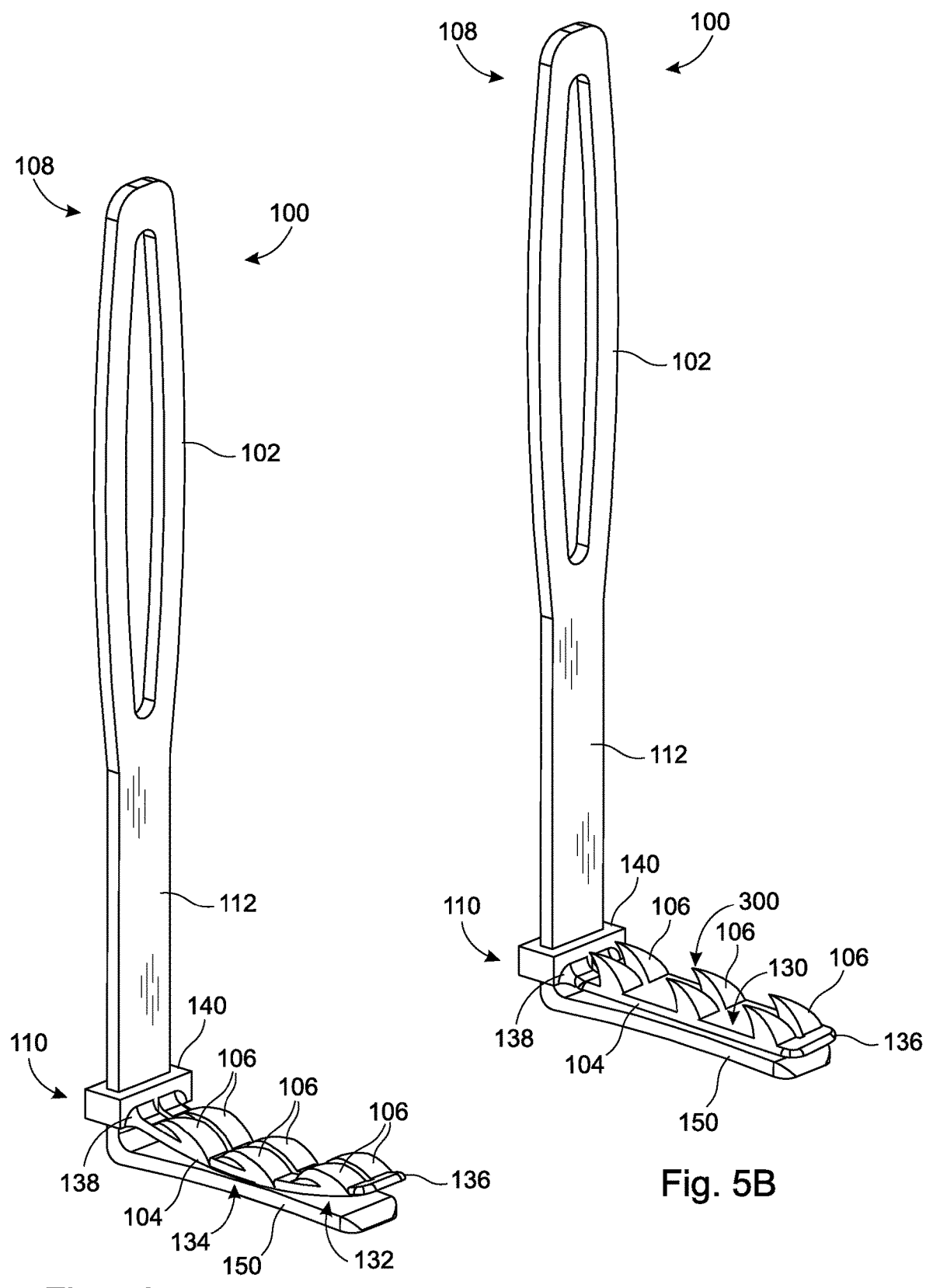
FIGS. 5A-5B show perspective views of another embodiment of a deployable surgical retractor in the stowed configuration and deployed configuration, respectively.

In some embodiments, as shown in FIGS. 5A and 5B, the blade 104 may comprise a slide bracket 140. The slide bracket 140 may be slidably attached to the neck 112. The handle 102 may be operatively connected to a support 150 that projects perpendicularly from the neck 112 at the proximal end 110. As in the previous embodiment, the blade 104 may have a first configuration in which the top surface 130 is concave and the retraction elements 106 are folded in a stowed position to prevent the retraction elements 106 from catching tissue or gloves as shown in FIG. 5A. Due to the concave top surface 130, the bottom surface 132 has a convex shape. As such, the middle portion 134 of the bottom surface 132 may be in contact with the support 150 while the ends (free end 136 and connected end 138) of the blade 104 pucker upwardly.

In use, when the blade 104 is applied against the tissue, the slide bracket 140 slides closer towards the proximal end 110 of the retractor 100 causing the blade 104 to flatten out since the middle section 134 of the blade 104 cannot move downwardly any further past the support 150. As the blade 104 flattens out, the tips 300 of the retraction elements 106 begin to expose themselves. In some embodiments, at some point, the blade 104 may lock in place with the tips of the retraction elements 106 exposed. The blade 104 can be locked in place once the top surface 130 adapts a flat configuration or the top surface 130 becomes convex and the bottom surface 132 becomes concave. To return the retraction elements 106 back to the stowed position, the user need only to press down on the middle section 134 on the top surface 130 to cause the top surface 130 of the blade 104 to return back to a concave configuration causing the retraction elements 106 to fold back towards the blade 104. Alternatively, the user can lift upwardly on the free end 136.

In some embodiments, the blade 104 may not lock in place in the deployed configuration. Rather, when the retractor 100 is first making contact with the tissue, the free end 136 of the blade 104 would first make contact with the tissue, then the user would pull away from the incision in a radial direction. That motion would allow the clearance needed to expose the retraction elements 106 to engage with the tissue. In addition, the pull force is not solely horizontal, but at a slight upward angle which would allow the retraction elements 106 to remain exposed and engaged with the tissue.

In some embodiments, as shown in FIGS. 6A-6C, the blade 104 may be curved having a concave top surface 130, a convex bottom surface 132, an attached end 138, and a free end 136 opposite the attached end 138. The blade 104 may have a hollow interior housing the retraction elements 106. The free end 136 may have an opening 142 through which the retraction elements 106 can protrude. In this embodiment, the retraction elements 106 comprise elongated bodies 105 having a base end 107 operatively connected to an actuator 202, preferably located on the handle, and a tip 300 opposite the base end 107 that defines the portion of the retraction element that catches the tissue. The elongated body 105 is dimensioned substantially similar to the hollow interior of the blade 104 to allow the retraction element 106 to slide within the housing such that the tip 300 can project out from the opening 142 at the free end 136 so as to be exposed in the deployed configuration, and retract into the blade 104 so as to be stowed or hidden.

In the preferred embodiment, each retraction element 106 has associated with it its own elongated body 105 so as to have the appearance of a claw. Similarly, the blade 104 may comprise a plurality of hollow fingers 104a-d, each finger housing a retraction element 106a-d. At the base end 107 of the elongated bodies 105 may be a retraction bar 144 connecting each elongated body 105 to one another so that the deployment and withdrawal of the retraction elements 106a-d are coordinated. The retraction bar 144 is operatively connected to an actuator 202 by a connecting element 220 so that movement of the actuator 202 causes movement of the retraction bar 144, which in turn causes movement of the retraction elements 106.

For example, the actuator 202 may be slidably connected to the handle 102 so as to allow the actuator 202 to move up and down. The actuator 202 may be connected to the retraction bar 144 by a connection element 220, such as a cable, a rod, and the like. Upward movement of the actuator 202 raises the retraction bar causing the retraction elements 106 to withdraw into the blade 104 simultaneously in the stowed configuration. Downward movement of the actuator 202 may cause the retraction elements 106 to deploy simultaneously so as to be exposed for use. In some embodiments, a spring 210 may be operatively connected to the retraction bar 144 to keep the retraction elements 106 in the stowed configuration. For example, the spring 210 may impart a biasing force against the base ends 107 of the retraction elements 106 so as to move the base ends 107 towards the actuator 202. This causes the tips 300 of the retraction elements 106 to retract into the blade. Sufficient force on the actuator 202 will have to be applied to overcome the spring 210 and cause the retraction elements 106 to be exposed. A locking mechanism 203, 205 may be used to keep the retraction elements 106 in the exposed configuration.

In some embodiments, a locking mechanism 203, 205 may be provided to allow the retraction elements 106 to remain in the deployed configuration during use without the user having to hold the actuator 202 in place. For example, the handle 102 may comprise a catch 205, such as an orifice, hook, and the like, through which a locking pin 203 on the actuator may be inserted when the retraction elements 106 are in the deployed configuration. A release button may be provided to release the locking pin 203 to allow the actuator 202 to revert back to its original position and bring the retraction elements 106 into a stowed configuration. This type of locking mechanism 203, 205, and other locking mechanisms, can be used in any embodiment with an actuator 202 described herein.

In some embodiments, the retraction bar 144 may be operatively connected to the actuator 202 through a stop bracket 146. The actuator 202 may be connected to the stop bracket 146 through a connection element, such as a rod, a cable, and the like. The stop bracket 146 may have a spring imparting a biasing force to keep the retraction elements 106 in the stowed configuration.

Figure 7A:
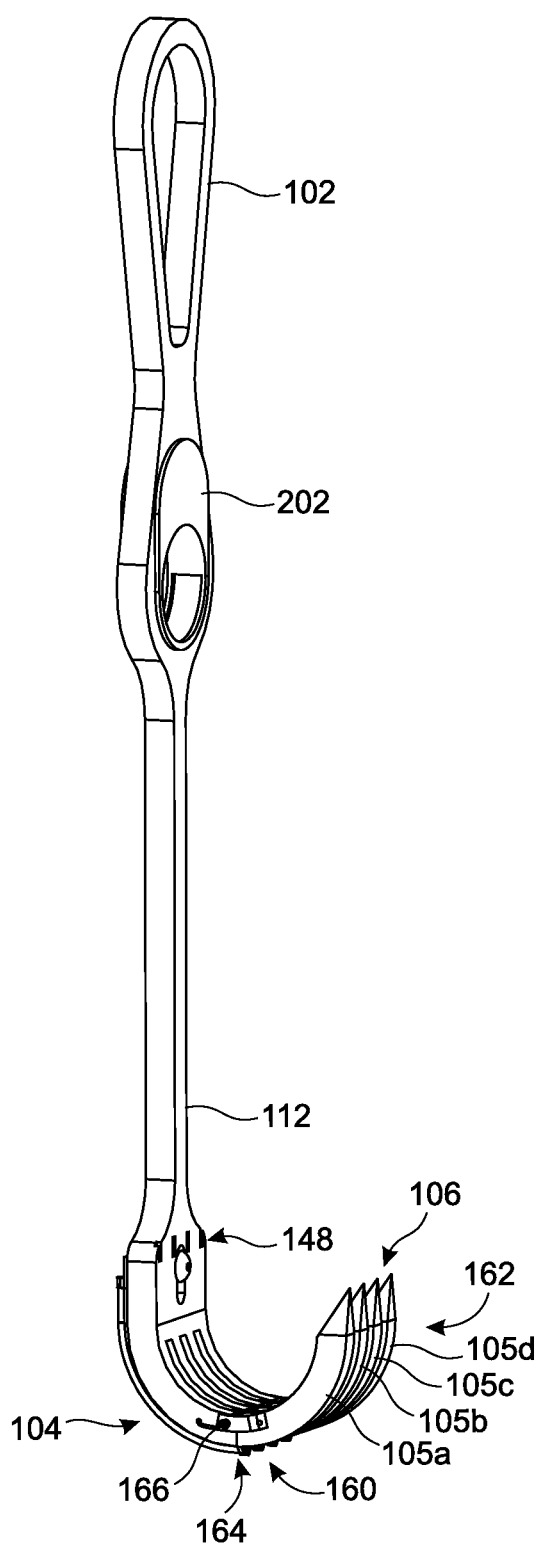
FIGS. 7A-7B show perspective views of another embodiment of a deployable surgical retractor in the deployed configuration and stowed configuration, respectively.
Figure 7B:
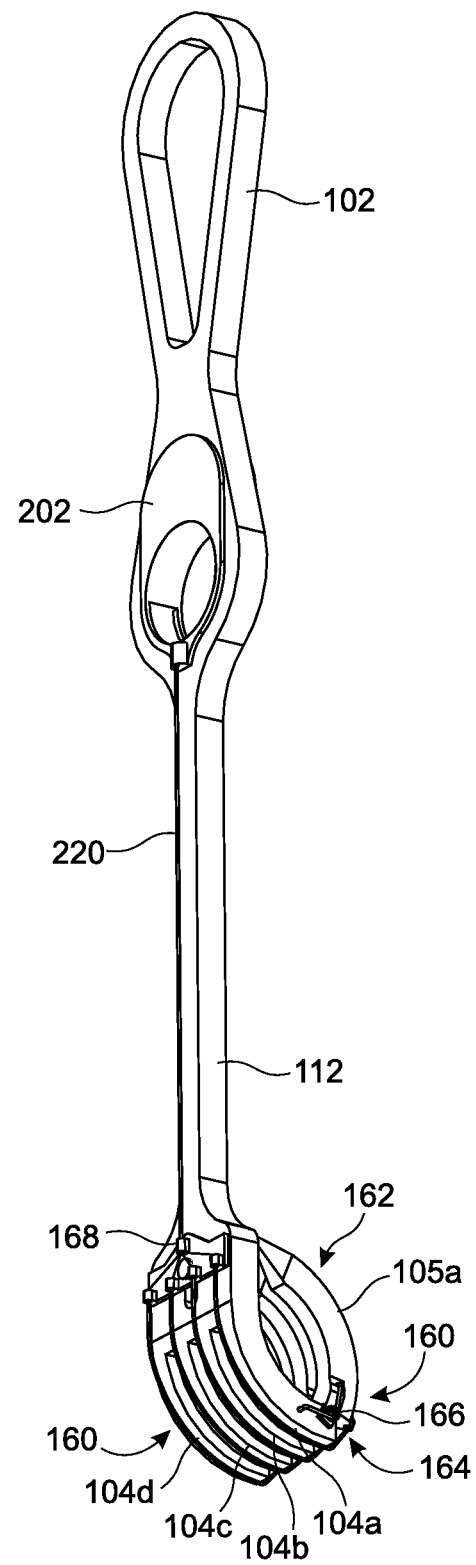
Figure 8A:
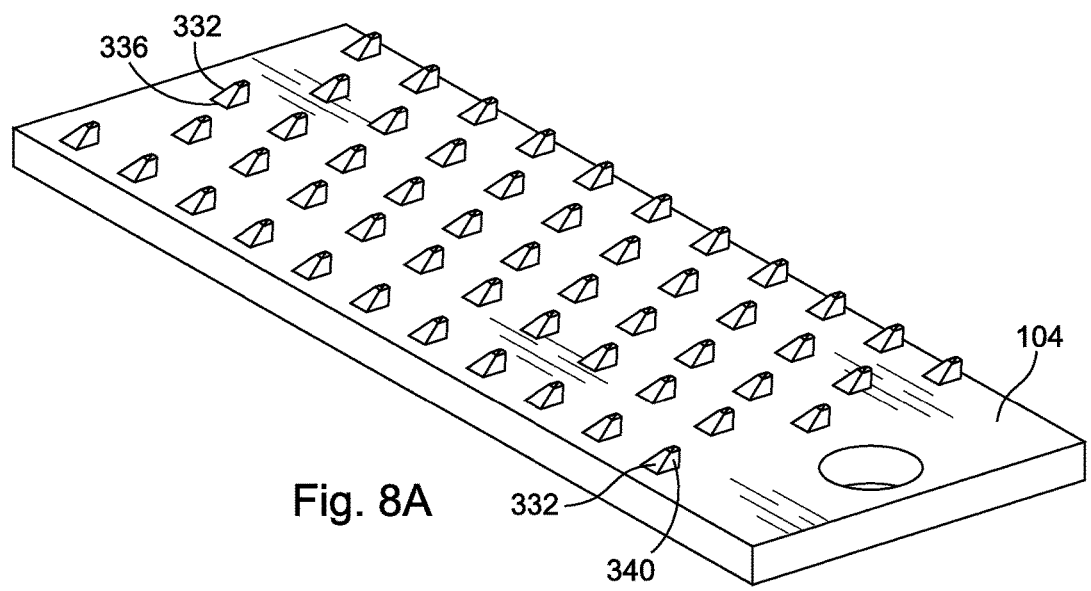
FIGS. 8A-8C show a perspective view, a top view, and a close-up side view taken through 8C shown in FIG. 8B, respectively, of an embodiment of a retraction surface with fixed retraction elements.
Figure 8B:
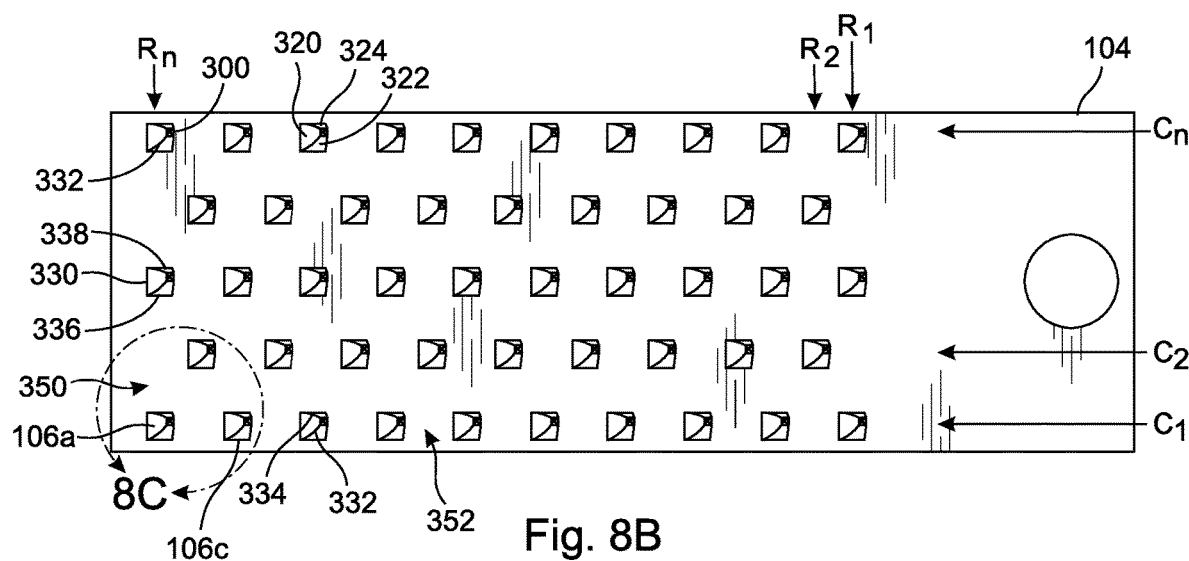
Figure 8C:
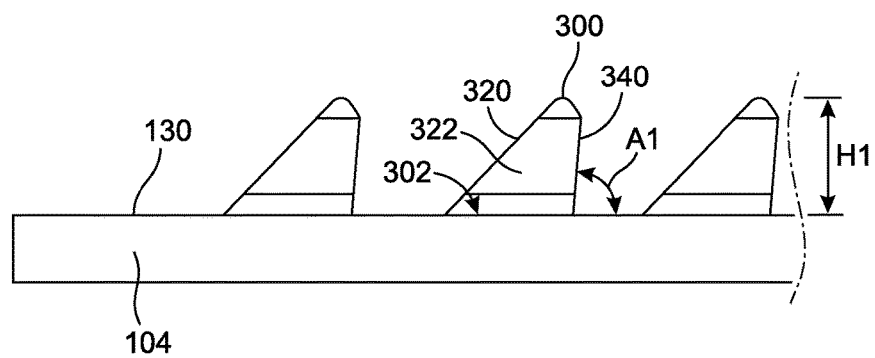

In some embodiments, as shown in FIGS. 7A-7B, the retraction elements 106 may be in the form of articulating elongated bodies 105a-d that can fold or bend at a joint or joints 164 to be in a stowed configuration. The retraction elements 106 may project out from the distal ends 162 of the elongated bodies 105a-d. The proximal end 160 of the elongated bodies 105a-d, may be attached to the blade 104. The proximal end 160 and the blade 104 may be connected at a joint 164. The joint 164 may have a spring 166 associated with it causing the retraction elements 106 to be biased towards the blade 104 as shown in FIG. 7B. In the preferred embodiment, the blade 104 may also be divided into separate elongated bodies 104a-d to correspond with the retraction elements 106.

In some embodiments, each retraction element 106 may be connected to one another so that one or more springs 166 can be used to move all of the retraction elements together in a coordinated manner. In some embodiments, multiple springs 166 may be used to move all of the retraction elements 106 together in a coordinated manner. In some embodiments, each retraction element 106 may have its own spring 166 and the actuator may be split so as to be able to retract and deploy each individual retraction elements separate and apart from the others.

The actuator 202 may comprise a connecting element 220, such as a cable, rod, and the like, extending down the neck 112 and wrapping around the blade 104 to connect with the retraction elements 106. The retraction elements 106 and blade 104 are curved such that when the retraction elements 106 are in the deployed state, the retraction elements 106 and the blade 104 form a semicircle or U-shape when viewed from the side. A cable guide 168 may be provided at the junction where the neck 112 meets the blade 104 to manage the connecting element 220 attached to the blade 104. Raising the actuator 202 causes the connecting element 220 to move away from the retraction elements 160 causing the distal end 162 of the retraction element 106 to rotate at the joint 164 to the deployed configuration. When the actuator 202 is released, the spring 166 causes the distal end 162 of the retraction elements 106 to revert back to its stowed configuration. In some embodiments, the top surface 130 of the blade 104 may have depressions 148 into which the tips 300 of the retraction elements 106 may be embedded to hide the tips 300 when not in use. In use, this action causes the retraction elements to "grip" the tissue.

In some embodiments, aside from the retraction elements 106 being deployable, the retraction elements 106 may be fixed, but arranged in a specific configuration that minimizes tearing of the gloves while still retaining the ability to grip and hold tissue during the surgical procedure.

For example, the retraction elements 106 may have an anisotropic configuration, such as an oblique pyramid comprising a base 302, a back wall 320, a first sidewall 322, a second sidewall 324, wherein the base 302 and the back wall 320 define a posterior edge 330, the back wall 320 and the first sidewall 322 define a first dorsolateral edge 332, the back wall 320 and the second sidewall 324 define a second dorsolateral edge 334, the base 302 and the first sidewall 322 define a first ventrolateral edge 336, the base 302 and the second sidewall 324 define a second ventrolateral edge 338, and the first sidewall 322 and the second sidewall 324 converge to define an anterior side 340 that is perpendicular to the posterior edge 330. In the preferred embodiment, the back wall 320 is triangular in shape and tapers moving from the posterior edge 330 towards the anterior side 340 and terminates at the tip 300 where the back wall 320 meets the anterior side 340. In addition, the back wall 320 may be ramped upwardly from the posterior edge 330 towards the anterior side 340. In some embodiments, the base 302 of the retraction element 106 may be rectangular so that the anterior side 340 defines an anterior surface as shown in FIGS. 8A-9C. However, circular, oval, triangular, pentagonal, and other geometric shapes can also be used for the base 302 in this embodiment and the embodiments discussed hereafter. In some embodiments, the base 302 of the retraction element 106 may be triangular so that the anterior side 340 defines and anterior edge (i.e. sharp edge or very narrow surface as shown in FIGS. 10A-13C).

In the preferred embodiment, the retraction elements 106 are evenly arranged in columns C1-Cn and rows R1-Rn. In some embodiments, the rows R1-Rn may be staggered so that retraction elements 106 in every other column are aligned in their respective rows. In some embodiments, spacing may exist between retraction elements 106. For example, the first column of retraction elements C1 and the second column of retraction elements C2 directly adjacent to the first column of retraction elements C1 may define a lateral gap 350 as shown in FIGS. 8A-12C. In some embodiments, the lateral gap 350 between the posterior edge 330 of a first column retraction elements C1 and a second column of retraction elements C2 may range from approximately 0 inch to approximately 0.1 inch. In some embodiments, the lateral gap 350 may be approximately 0.03 inch to approximately 0.07 inch.

Figure 13A:
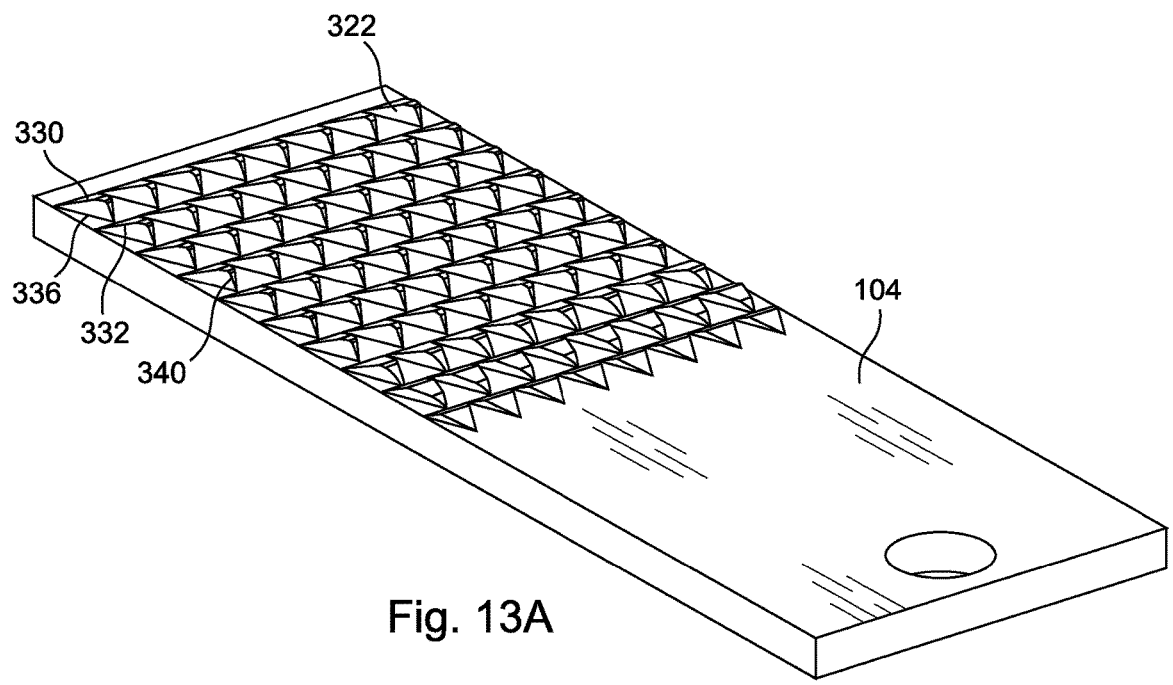
FIGS. 13A-13C show a perspective view, a top view, and a close-up side view of 13C shown in FIG. 13B, respectively, of another embodiment of a retraction surface with fixed retraction elements.
Figure 13B:
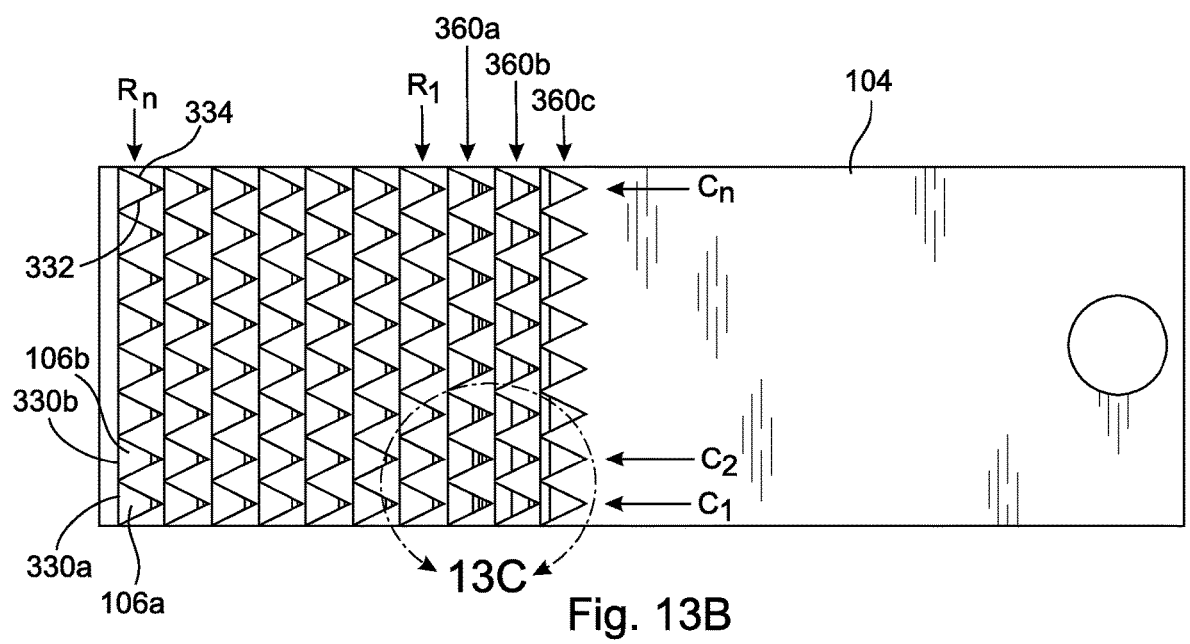
Figure 13C:
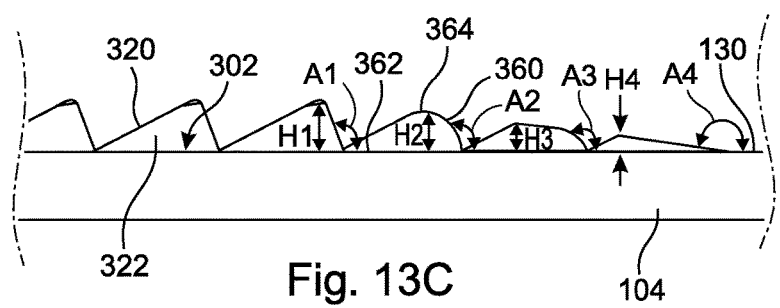

In some embodiments, the spacing arrangement in between retraction elements 106 may be tight or non-existent. For example, as shown in FIG. 13B, the posterior edge 330a of a retraction element 106a in a first column of retraction elements C1 may touch the posterior edge 330b of a second retraction element 106b in a second column of retraction elements C2 directly adjacent to the first column of retraction elements C1.

An anterior angle A1 defined by the anterior side 340 and the top surface 130 of the blade 104 may range from approximately 60 degrees to approximately 120 degrees. Preferably, the anterior angle A1 is approximately 75 degrees to approximately 105 degrees. In some embodiments, the anterior angle A1 may be approximately 80 degrees to approximately 110 degrees. In one embodiment, the anterior angle A1 is approximately 85 degrees.

Figure 11A:
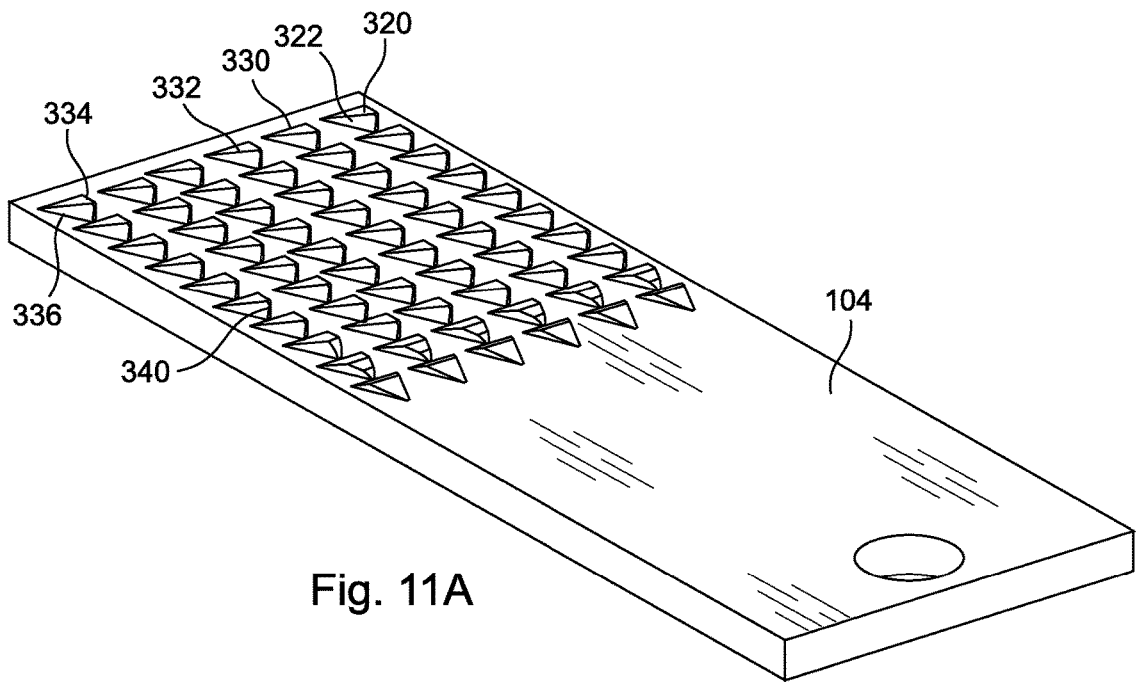
FIGS. 11A-11C show a perspective view, a top view, and a close-up side view of 11C shown in FIG. 11B, respectively, of another embodiment of a retraction surface with fixed retraction elements.
Figure 11B:
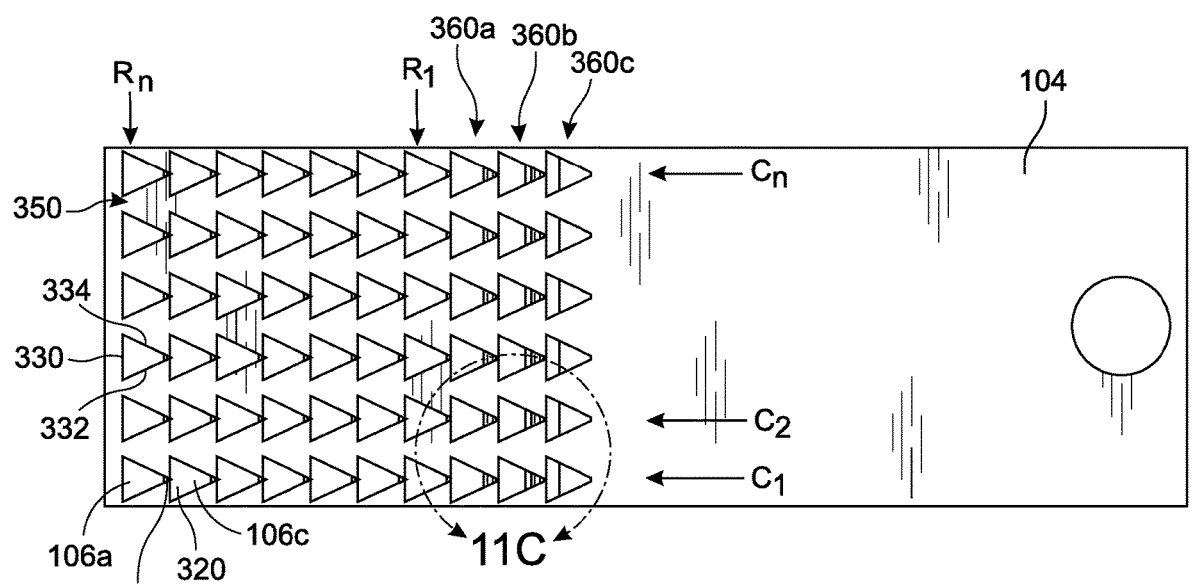
Figure 11C:
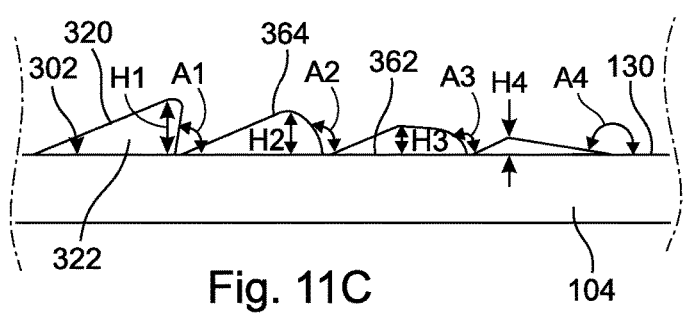

In embodiments in which the anterior angle A1 defines an acute angle, the tip 300 of a first retraction element 106a may overlap with the back wall 320 of a second retraction element 106c directly in front of the first retraction element 106a when viewed from the top as shown in FIG. 11B. In some embodiments, there may be an anterior-posterior gap 352 between the anterior side 340 at the base 302 of a first retraction element 106a and the back wall 320 or posterior edge 330 of a second retraction element 106c directly in front of the first retraction element 106a when viewed from the top. By way of example only, the anterior-posterior gap 352 between the anterior portion of the base of a first retraction element 106a and the posterior edge 330 of a second retraction element 106c directly in front of the first retraction element 106a may range from 0 inch to approximately 0.5 inch. Preferably, anterior-posterior gap 352 may be approximately 0.1 inch to approximately 0.4 inch.

The height H1 of the retraction elements 106 as measured from the base 302 to the tip 300 is at most approximately 0.1 inch high. Preferably, the height H1 may be approximately 0.0395 inch to approximately 0.1 inch. More preferably, the height H1 may be approximately 0.05 inch to 0.075 inch. Even more preferably, the height H1 is 0.0625 inch.

The tips 300 may range from being flat, to rounded, to sharp points. Flat tips define a top that has a planar surface that is parallel to the top surface of the blade. A rounded tip has a radius ranging from approximately 0.005 inch to approximately 0.02 inch. More preferably, the radius is approximately 0.01 inch to approximately 0.015 inch.

In some embodiments, the surgical retractor 100 may comprise a plurality of barrier elements 360 aligned anterior to a first row R1 of retraction elements 106. In some embodiments, the barrier elements 360 may be non-sharp projections from the blade 104. For example, each barrier element 360 may be in the shape of a semi-cylinder with the flat base 362 of the semi-cylinder attached to the blade 104, and the curved surface 364 of the cylinder projecting upwardly, away from the blade 104.

In some embodiments, as shown in FIGS. 10A-11C, the surgical retractor 100 may comprise a plurality of rows of barrier elements 360a-c aligned anteriorly to the retraction elements 106, each row of barrier elements defining a height H2-H4 of the row of barrier elements 360a-c, wherein the height H2-H4 of each row of barrier elements 360 progressively decreases moving away from the retraction elements 106. Therefore, the row of barrier elements 360a directly adjacent to the anterior-most row of retraction elements 106 may have a height H2 substantially equivalent to, slightly larger than, or slightly smaller than the height H1 of the retraction elements 106. Moving away from the retraction elements 106, the next row of barrier elements 360b decreases in height H3. In other words, the heights H2-H4 of each row of barrier elements 360a-c progressively decreases moving away from the retraction elements 106.

Corresponding with the decrease in the height H2-H4 of each row of barrier elements 360a-c may be a decrease in the sharpness of the top portions 364 of the barrier elements 360. In other words, as the height of the barrier elements 360 increases moving towards the retraction elements 106, the sharpness of the top portion 364 of the barrier elements 360 also increases so as to look more and more like the retraction element 106. Therefore, the barrier elements 360 may actually be incompletely formed retraction elements 106. In particular, the barrier elements 360 may be retraction elements 106 with incompletely formed top portions 364.

Therefore, in some embodiments the front angle A4 of the anterior-most barrier elements 360c may be extremely obtuse ranging from approximately 175 degrees to approximately 155 degrees. Moving towards the retraction elements 106, the next row of barrier elements 360b may have a front angle A3 ranging from approximately 155 degrees to approximately 135 degrees. Continuing to move towards the retraction elements 106, the next row of barrier elements 360a may have a front angle A2 ranging from approximately 135 degrees to approximately 110 degrees.

In some embodiments, the anterior side 340 of the barrier elements 360 may be curved or convex in shape. Moving from the anterior-most barrier elements 360c towards the retraction elements 106, the degree curvature of the anterior side 340 may decrease thereby defining a large radius of curvature.

In some embodiments, the surgical retractor 100 may further comprise two columns of side barrier elements 370, 372 bilaterally arranged on opposite sides of the retraction elements 106. As shown in FIGS. 10A-10C and 12A-12C, each column of side barrier elements 370, 372 may have lateral faces 374, 376 facing away from the retraction elements 106. The lateral faces 374, 376 may be ramped upwardly towards the retraction elements 106. Therefore, the lateral faces 374, 376 on the blade 104 may make a lateral face angle L of approximately 110 degrees to approximately 155 degrees. Similarly, the medial faces 378, 380 of the column of side barrier elements 370, 372 facing the retraction elements 106 may have medial face angles M defined by the medial face 370, 372 of the barrier elements 360 and the blade 104 of approximately 110 degrees to approximately 155 degrees. In some embodiments, the medial faces 370, 372 may be curved.

Figure 9A:
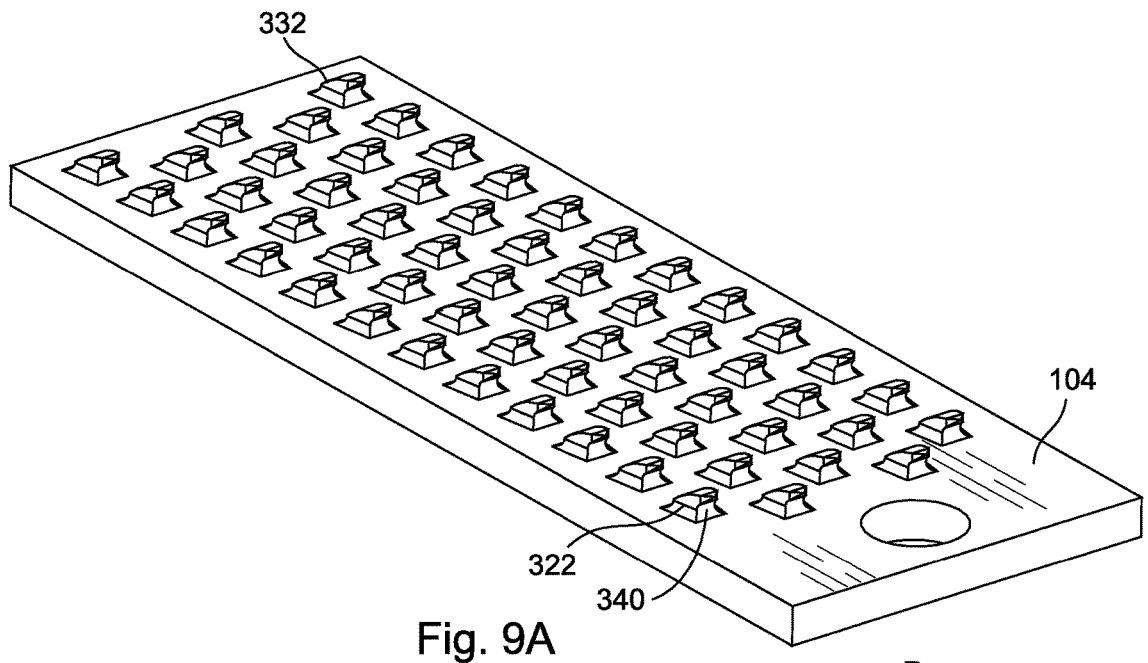
FIGS. 9A-9C show a perspective view, a top view, and a close-up side view of 9C shown in FIG. 9B, respectively, of another embodiment of a retraction surface with fixed retraction elements.
Figure 9B:
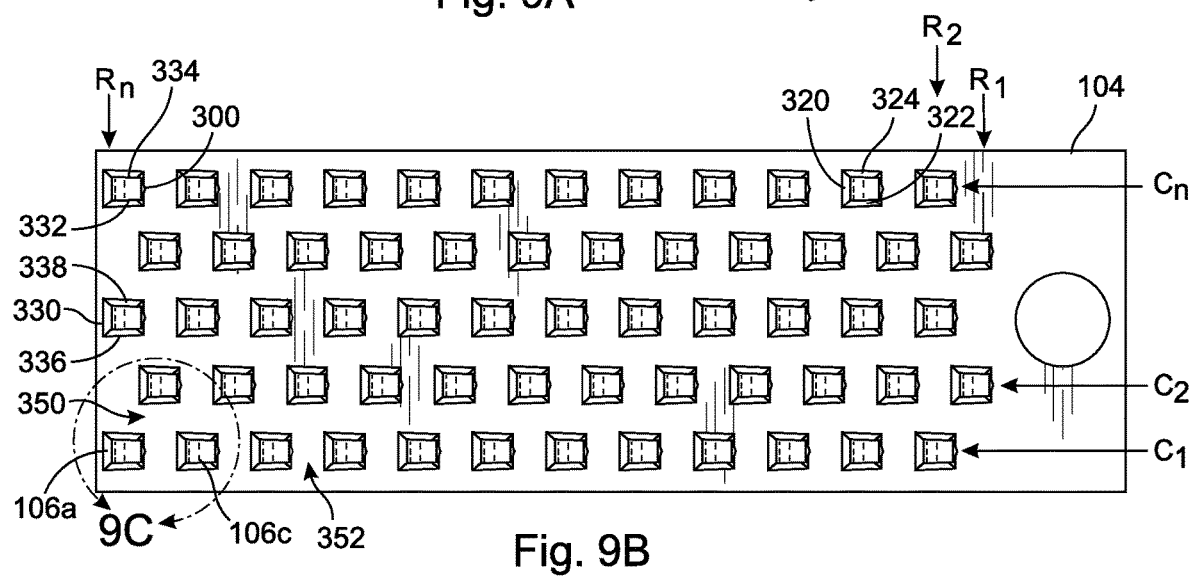
Figure 9C:
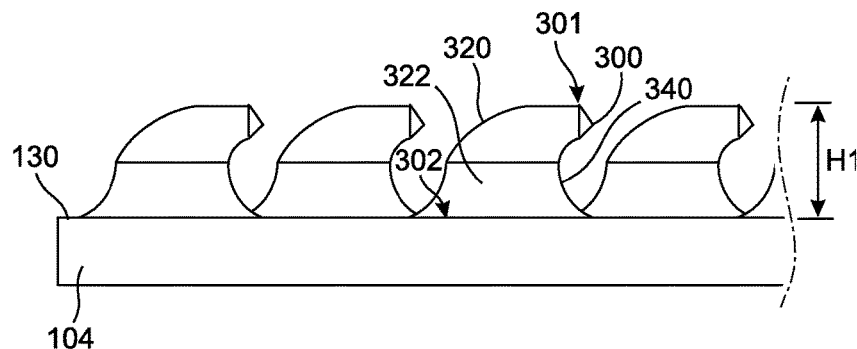
Figure 10A:
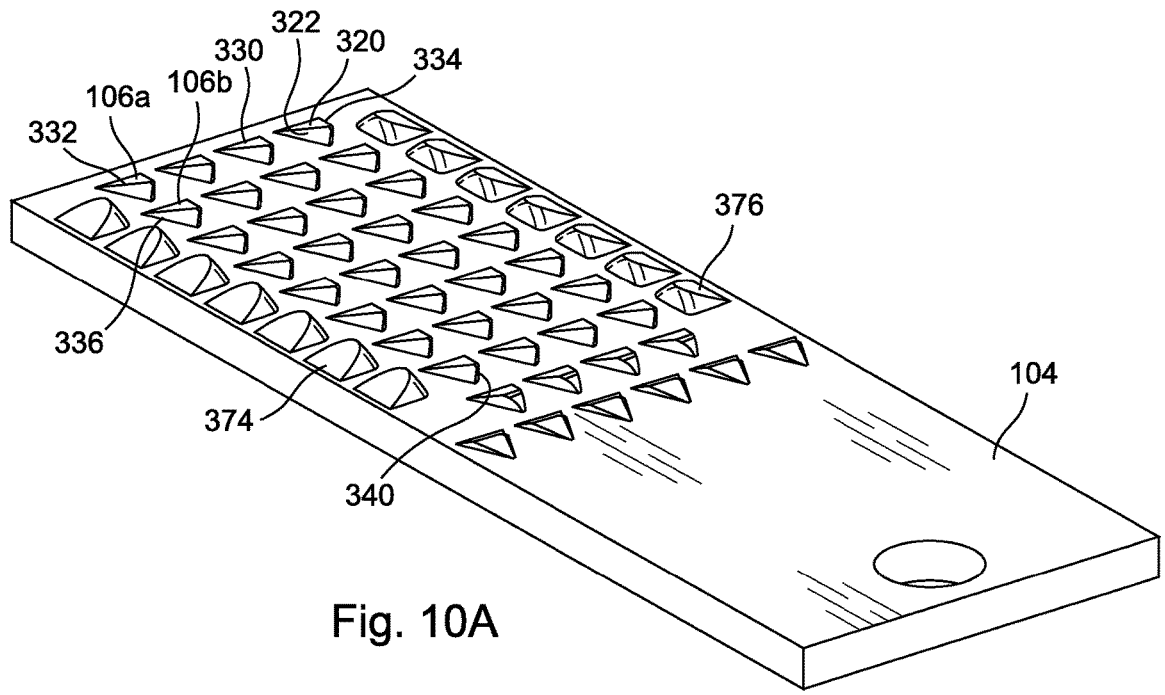
FIGS. 10A-10C show a perspective view, a top view, and a close-up side view of 10C shown in FIG. 10B, respectively, of another embodiment of a retraction surface with fixed retraction elements.
Figure 10B:
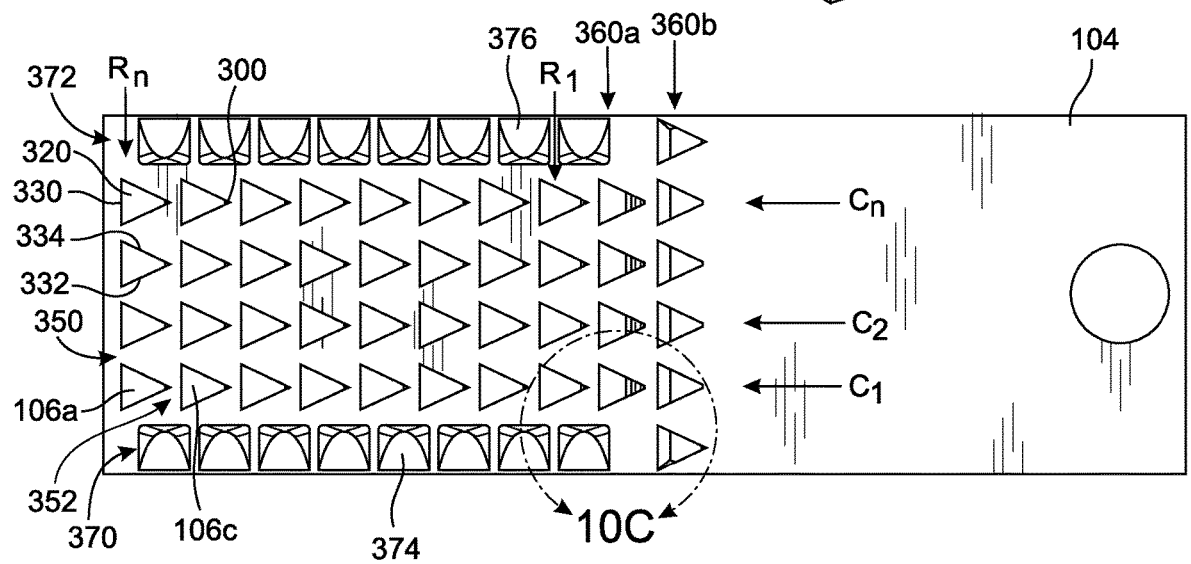
Figure 10C:
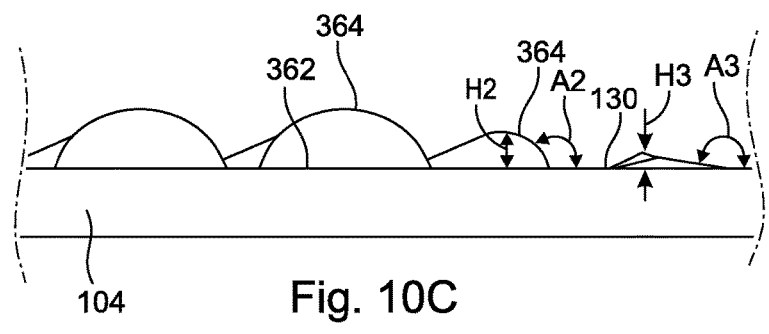

In some embodiments, the retraction elements 106 may have a concave anterior side 340 causing the tip 300 to project in the anterior direction generally parallel to the blade 104 as shown in FIGS. 9A-9C. This is referred to as the hook shaped retraction element. In the preferred embodiment, the base 302 is rectangular in shape. However, circular, oval, triangular, pentagonal, and other geometric shapes can also be used for the base 302 in any of these embodiments. As the back wall 320 rises away from the base 302, the back wall 320 curves towards the anterior side 340. Thus, the back wall 320 is convex in shape. The anterior side 340 is similarly curved, but defines a concave surface. As the back wall 320, the anterior side 340, and opposing sidewalls 322, 324 move away from the base 302 in their respective curved manner, they begin to converge towards each other and form a rectangular base 301 for the tip 300. The rectangular base 301 is substantially perpendicular to the top surface 130 of the blade 104. From the rectangular base 301, the tip 300 converges to a sharp point forming a rectangular pyramid pointing in a direction parallel to the top surface 130 of the blade 104.

In any of the fixed retraction element 106 embodiments, the retraction elements 106 may be evenly arranged in columns C1-Cn and staggered rows R1-Rn so that retraction elements 106 in every other column are aligned in their respective rows.

Figure 14A:
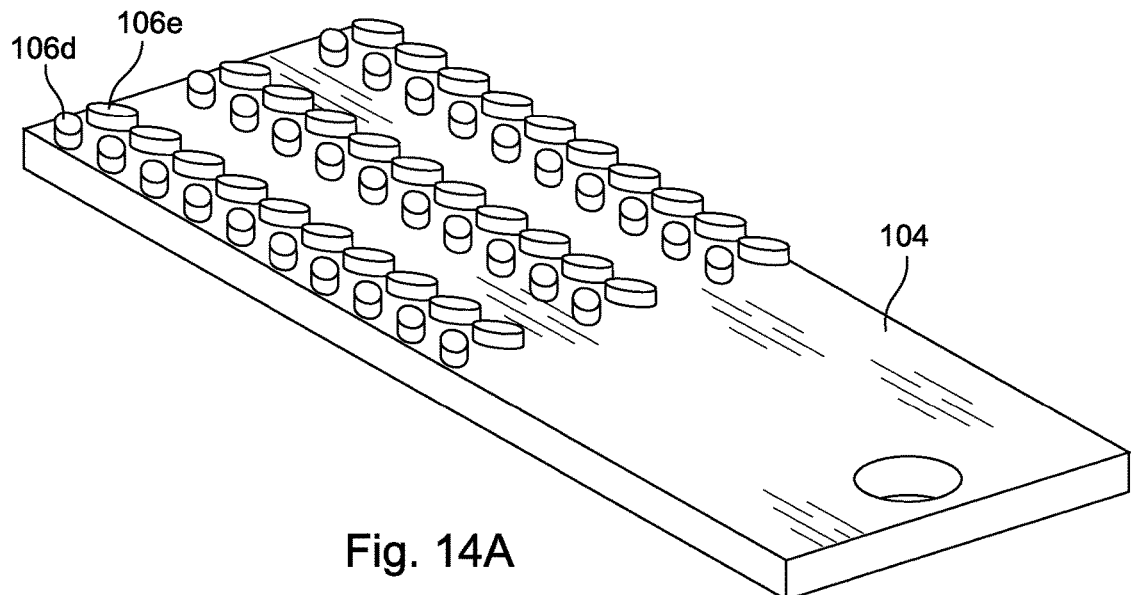
FIGS. 14A-14C show a perspective view, a top view, and a close-up side view of 14C shown in FIG. 14B, respectively, of another embodiment of a retraction surface with fixed retraction elements.
Figure 14B:
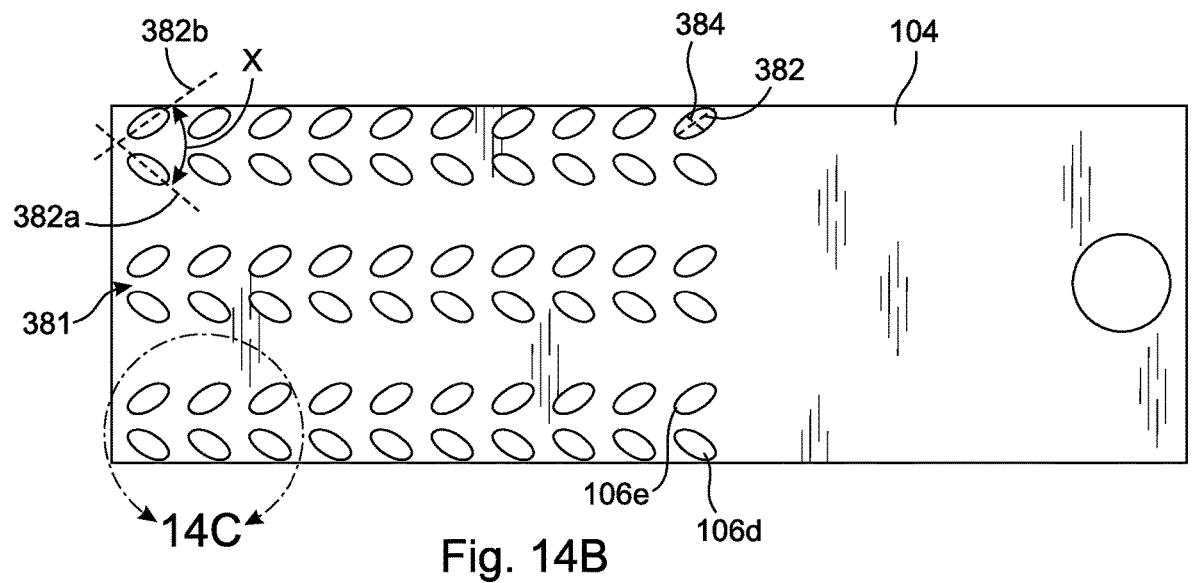
Figure 14C:
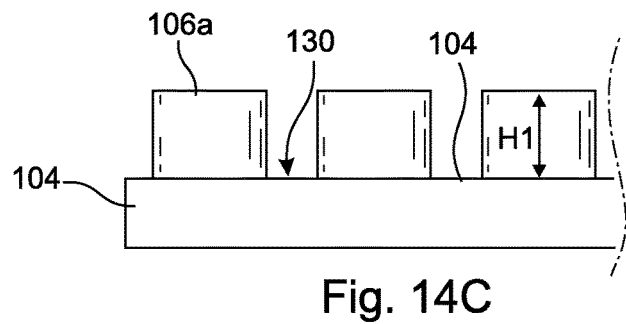

In some embodiments, the retraction elements 106 are arranged in pairs. As shown in FIGS. 14A-14C, in some embodiments, the retraction elements 106 may comprise a plurality of columns of paired posts 106d, 106e. The individual posts 106e, 106e within a pair may be separated by a minimum distance 381 of approximately 0.02 inch to approximately 0.07 inch. Preferably the minimum distance 381 is approximately 0.03 inch to approximately 0.06 inch. Most preferably, the minimum distance 381 is 0.04 inch to 0.05 inch. In one embodiment, the minimum distance 381 between two posts is 0.045 inch. The posts 106d, 106e may range from approximately 0.0395 inch to approximately 0.1 inch in height H1. The tops of the posts 106d, 106e may be flat or round. Paired post embodiments work by trapping tissue in between the pair of posts 106d, 106e without having to rely on sharp edges. In other words, tissue become wedged in between the individual posts 106d, 106e of the paired post.

In some embodiments, to improve the ability of the paired posts 106d, 106e to catch tissue, the individual posts 106d, 106e may be oval in shape when viewed from the top, the oval defining a major axis 382 and the minor axis 384 perpendicular to and smaller than the major axis 382. In addition, the posts 106d, 106e within a pair may be angled relative to each other so that their respective major axes 382a, 382b define an angle. The major axes angle X between paired posts 106d, 106e may be greater than 0 degree to less than 180 degrees. Preferably, the major axis angle X ranges from approximately 30 degrees to approximately 150 degrees, and any angle therebetween. More preferably, the major axis angle X ranges from approximately 45 degrees to approximately 135 degrees, and any angle therebetween. Even more preferably, the major axis angle X ranges from approximately 60 degrees to approximately 120 degrees, and any angle therebetween. In some embodiments, the major axis angle X may be 70 degrees, 80 degrees, 90 degrees, 100 degrees, or 110 degrees, or any angle therebetween.

Figure 15A:
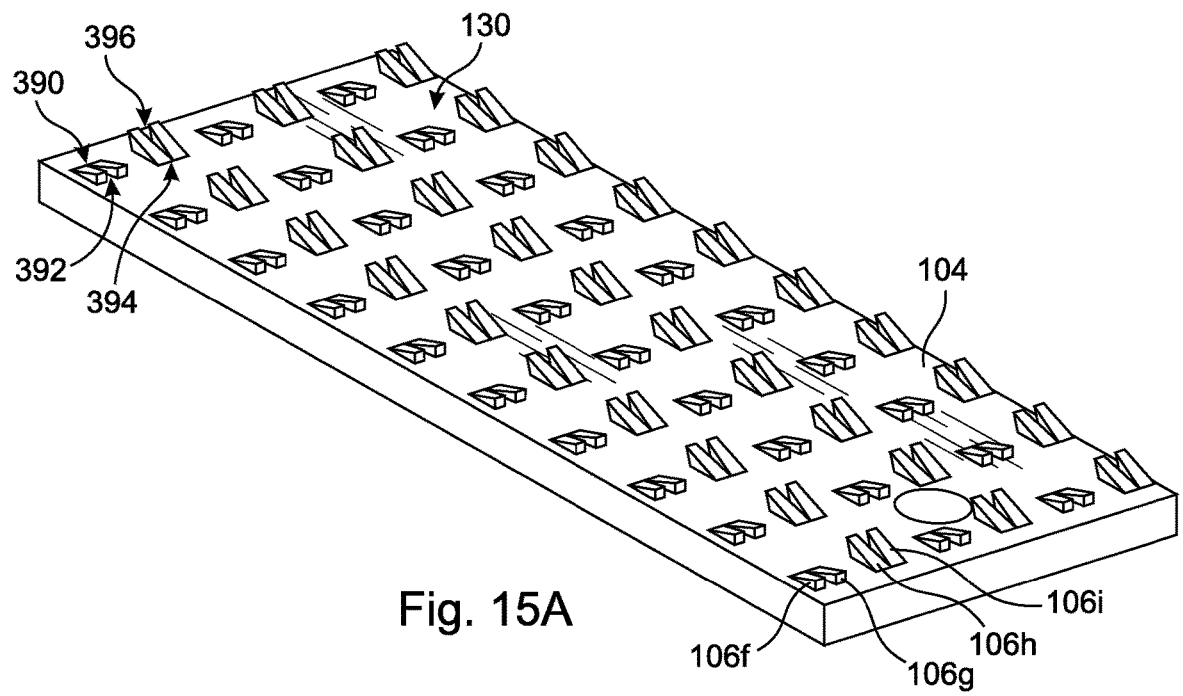
FIGS. 15A-15C show a perspective view, a top view, and a close-up side view of 15C shown in FIG. 15B, respectively, of another embodiment of a retraction surface with fixed retraction elements.
Figure 15B:
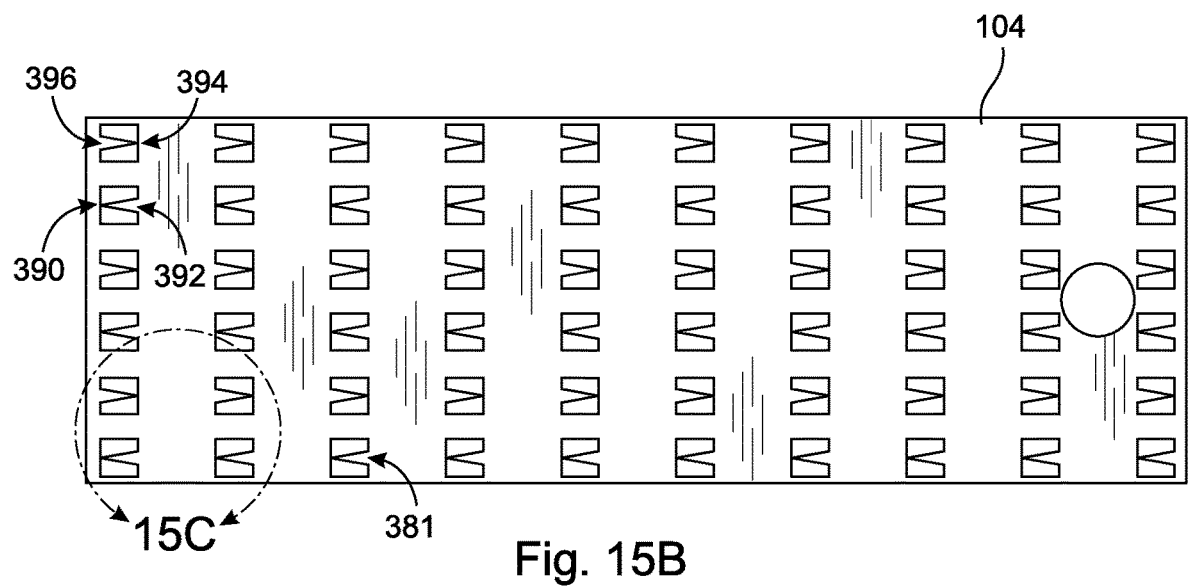
Figure 15C:
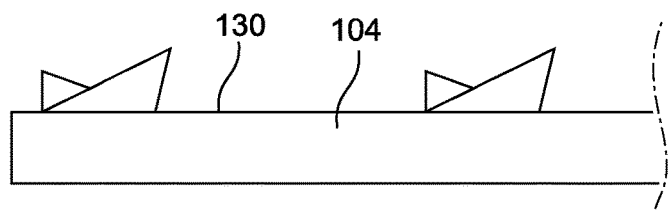

As shown in FIGS. 15A-15C, in some embodiments, the retraction elements 106 may comprise columns of smaller ramp pairs 106f, 106g and columns of larger ramped pairs 106h, 106i arranged in an alternating manner across the blade 104 defining rows of alternating smaller ramp pairs 106f, 106g and larger ramp pairs 106h, 106i. Each of the smaller ramp pairs 106f, 106g comprises a first ramped tooth 106f and a second ramped tooth 106g, wherein the ramped teeth 106f, 106g increase in height from a first end 390 to a second end 392. Thus, the first end 390 may be flush with the top surface 130 of the blade 104 while the second end 392 is elevated above the top surface 130 of the blade 104.

Similarly, each of the larger ramp pairs 106h, 106i comprises a first ramped tooth 106h and a second ramped tooth 106i, wherein the ramped teeth 106h, 106i increase in height from a first end 394 to a second end 396. Thus, the first end 394 may be flush with the top surface 130 of the blade 104 while the second end 396 is elevated above the top surface of the blade 104. The second ends 396 of the larger ramp pairs 106h, 106i are higher than the second ends 392 of the smaller ramped pairs 106f, 106g. In addition, the smaller ramped pairs 106f, 106g and the larger ramped pairs 106h, 106i face in opposite directions. Therefore, since smaller ramped pairs 106f, 106g and larger ramped pairs 106h, 106i are alternatingly arranged across a row, the first ends 390 of the smaller ramped pairs align with the second ends 396 of the larger ramped pairs across a row, and the second ends 392 of the smaller ramped pairs align with the first ends 394 of the larger ramped pairs across the row.

In between the ramped teeth of any ramp pair is a gap 381. In the preferred embodiment, the gap 381 diminishes from the second end 392, 396 to the first end 390, 394. The gaps 381 space between laterally adjacent ramped teeth open in opposite directions since the gap 381 in the smaller ramped pair 106f, 106g faces the opposite direction compared to the gap 381 in the larger ramped pair 106h, 106i.

Figure 16A:
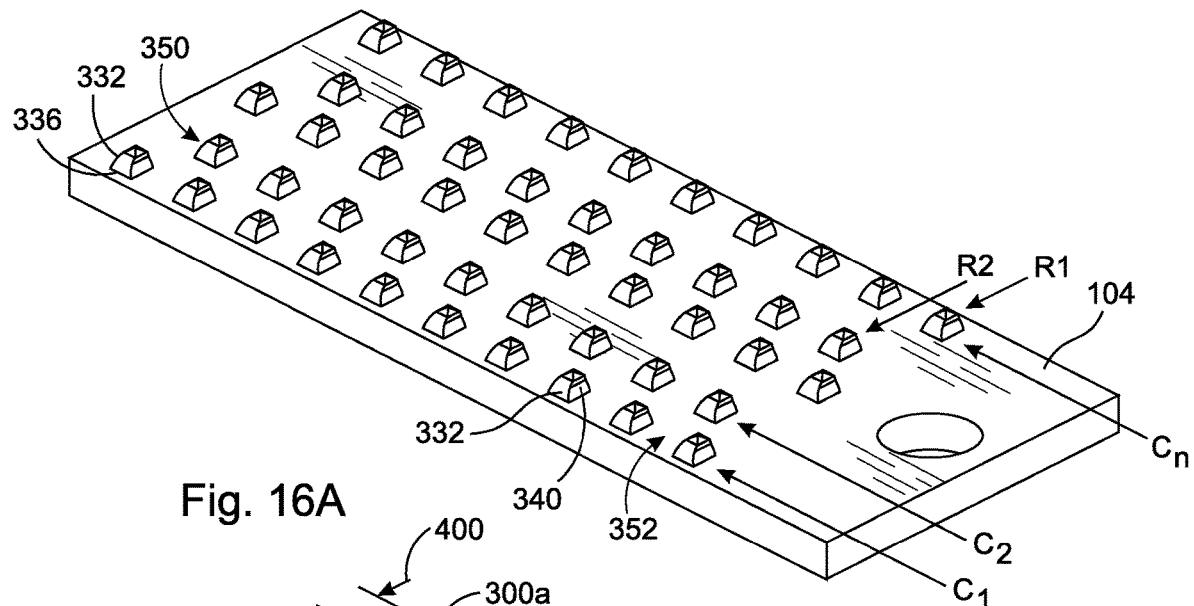
FIG. 16A shows a perspective view of another embodiment of the present invention with fixed retraction elements arranged in a staggered configuration.
Figure 16B:
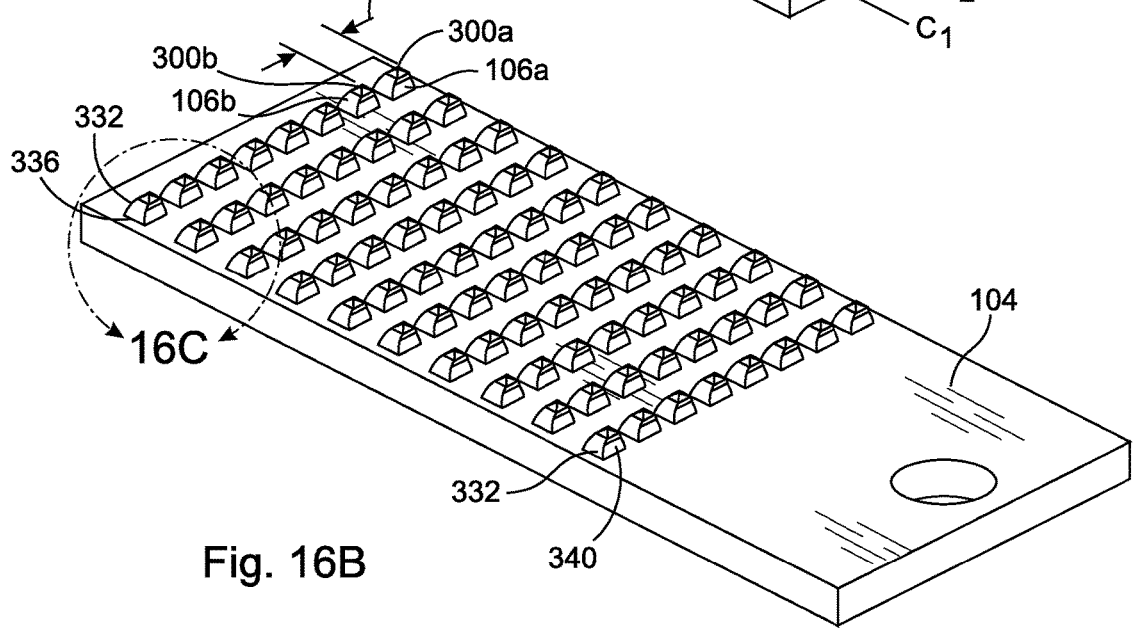
FIG. 16B shows a perspective view of another embodiment of the present invention with the retraction elements shown in FIG. 16A, but arranged in a linear configuration.
Figure 16C:
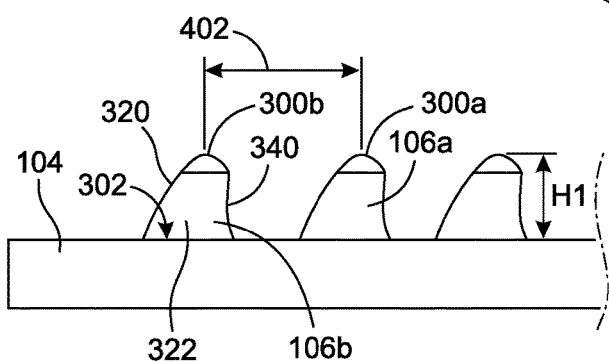
FIG. 16C shows a close-up side view of 16C shown in FIG. 16B.
Figure 18A:
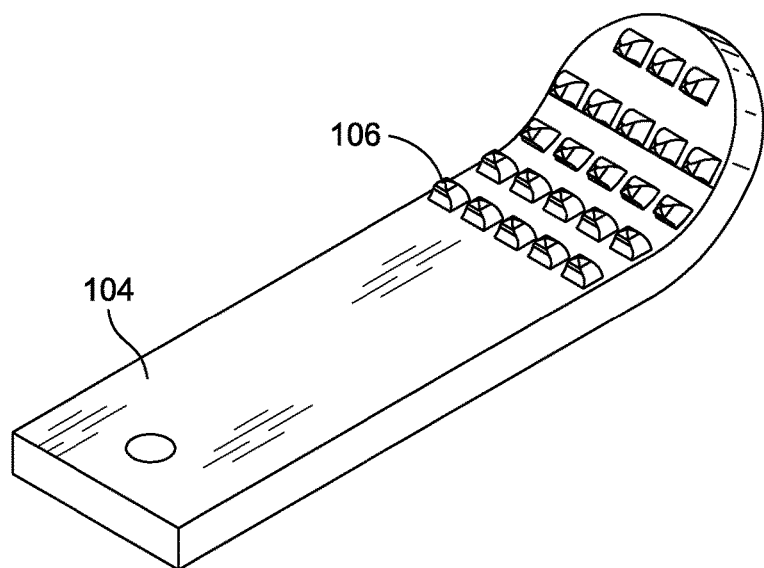
FIG. 18A shows an embodiment of the retraction elements from FIG. 16A as applied to an Army Navy-type surgical retractor.
Figure 18B:
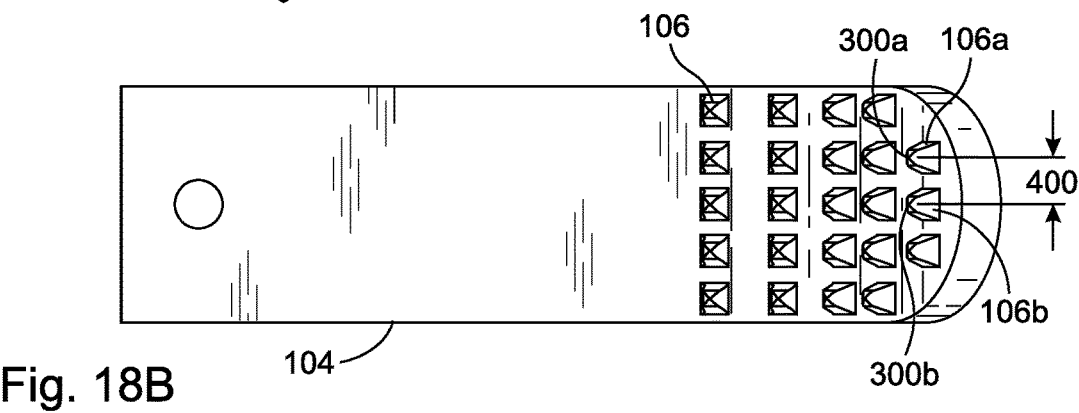
FIG. 18B is a top view of the embodiment in FIG. 17A.
Figure 18C:
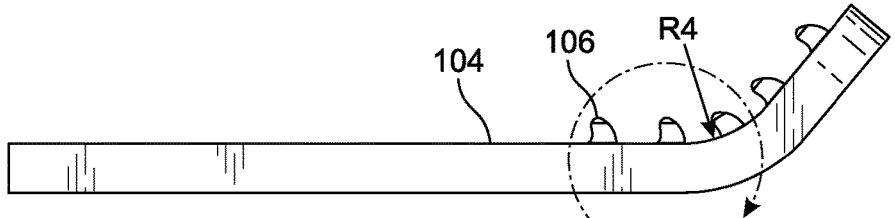
FIG. 18C is a side view of the embodiment in FIG. 17A.
Figure 18D:
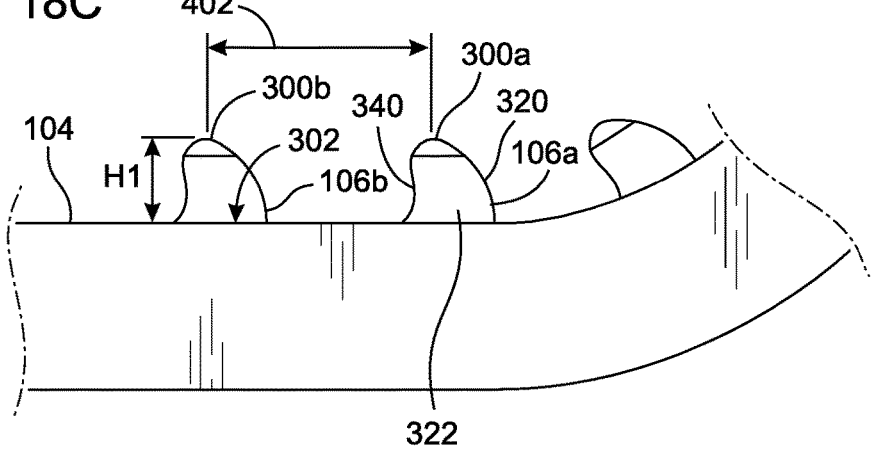
FIG. 18D is a close-up of the area indicated as 18D in FIG. 18C.

As shown in FIGS. 16A-16C, another oblique pyramid type of retraction element 106 has a recurved conical tooth shape defined by a generally rectangular base, which includes squares, with the anterior side 340 and the back wall 320 curving in the same direction, although not necessarily with the same degree of curvature, and terminating at a curved tip 300. However, circular, oval, triangular, pentagonal, and other geometric shapes can also be used for the base 302.

The base of the recurved conical tooth may have a width ranging from about 0.06 inch to about 0.10 inch. Preferably, the width is approximately 0.07 inch to approximately 0.09 inch. Most preferably, the width is approximately 0.08 inch. The length is approximately 0.05 inch to approximately 0.10 inch. Preferably, the length is approximately 0.06 inch to approximately 0.09 inch. Most preferably, the length is approximately 0.07 inch to approximately 0.08 inch.

The height H1 may range from approximately 0.05 inch to approximately 0.075 inch. Preferably, the height H1 is approximately 0.06 inch to approximately 0.07 inch. Most preferably, the height H1 is 0.065 inch.

The radius of curvature of the anterior side 340 ranges from approximately 0.030 inch to approximately 0.08 inch. Preferably, the radius of curvature of the anterior side 340 is approximately 0.04 inch to approximately 0.075 inch. In some embodiments, the radius of curvature of the anterior side 340 is approximately 0.06 inch to approximately 0.07 inch. In one example, the radius of curvature of the anterior side 340 was 0.0404 inch. In another example, the radius of curvature of the anterior side 340 was 0.0644 inch.

The radius of curvature of the back wall 320 ranges from approximately 0.05 inch to approximately 0.15 inch. Preferably, the radius of curvature of the back wall 320 ranges from approximately 0.07 inch to approximately 0.14 inch. In one example, the radius of curvature of the back wall 320 was 0.0708 inch. In another example, the radius of curvature was 0.1384 inch.

The tip 300 may be defined by two different radii of curvatures. One radius of curvature (referred to as the anteroposterior radius of curvature) defines the curvature of the tip 300 from the anterior side 340 to the back wall 320. The second radius of curvature (referred to as the lateral radius of curvature) defines the curvature of the tip 300 from the first sidewall 322 to the second sidewall 324.

The anteroposterior radius of curvature ranges from approximately 0.01 inch to approximately 0.025 inch. Preferably, the anteroposterior radius of curvature ranges from approximately 0.015 inch to approximately 0.02 inch. In one example, the anteroposterior radius of curvature was 0.0174 inch.

The lateral radius of curvature ranges from approximately 0.02 inch to approximately 0.035 inch. Preferably, the lateral radius of curvature ranges from approximately 0.025 inch to approximately 0.03 inch. Most preferably, the lateral radius of curvature is approximately 0.0272 inch.

The spacing in between each retraction element 106 may also play a role in the ability of the surgical retractor to grasp tissue without tearing the tissue or gloves. In some embodiments, as shown in FIG. 16A, the retraction elements 106 may be staggered so that adjacent columns of retraction elements are offset. Therefore, the retraction elements 106 in every other column are aligned in a single row. In other embodiments, as shown in FIG. 16B the retraction elements are linearly aligned to form a uniform grid of retraction elements 106.

In embodiments in which the retraction elements 106 are linearly aligned to form a uniform grid, the lateral tip distance 400, as measured from the tip 300a of a first retraction element 106a to the tip 300b of a second retraction element 106b immediately, laterally adjacent to the first retraction element 106a, ranges from approximately 0.08 inch to approximately 0.25 inch. Preferably, the lateral tip distance 400 ranges from approximately 0.10 inch to approximately 0.22 inch. In one example, the lateral tip distance 400 was 0.120 inch. In another example, the lateral tip distance 400 was 0.2100 inch.

The anteroposterior tip distance 402, as measured from the tip 300a of a first retraction element 106a to the tip 300b of a second retraction element 106b immediately, anteriorly or posteriorly adjacent to the first retraction element 106a, ranges from approximately 0.10 inch to approximately 0.20 inch. In the preferred embodiment, the anterior posterior tip distance 402 ranges from approximately 0.12 inch to approximately 0.18 inch. Most preferably, the anteroposterior tip distance 402 ranges from approximately 0.12 inch to approximately 0.13 inch. In one example, the anteroposterior tip distance was 0.1206 inch. In another embodiment, the anteroposterior tip distance 402 was 0.1219 inch. In another embodiment, the anteroposterior tip distance 402 was 0.1311 inch. In another embodiment, the anteroposterior tip distance 402 was 0.1750 inch.

In the staggered embodiments, a second column C2 of retraction elements 106 adjacent to a first column C1 of retraction elements 106 may be shifted in the anteroposterior direction by a distance that is approximately half the distance of the anteroposterior gap 352 or the anteroposterior tip distance 402. Another way of considering the staggered embodiment is that a second row R2 of retraction elements 106 adjacent to a first row R1 of retraction elements 106 may be shifted in the lateral direction by a distance that is approximately half the distance of the lateral gap 350 or the lateral tip distance 400.

Due to the configuration of the retraction elements 106, the retraction elements can still grasp the tissue without tearing through the tissue. In addition, the retraction elements 106, having tapered or rounded tips, prevent the tips from snagging onto gloves or tissue. The dispersed layout of each individual retraction element 106 discourages force distribution amongst the retraction elements 106 when in contact with the tissue. This allows for the retraction elements 106 to fully engage with the tissue. The tips 300 of the retraction elements 106 can be much more pronounced because the retraction elements 106 will not be able to snag or tear gloves.

In one example, as shown in FIGS. 17A-D, the recurved conical tooth embodiment is applied to the Volkman surgical retractor. The Volkman surgical retractor has a rake-like appearance wherein the blade is separated into individual fingerlike blades 104a-d. Therefore each blade 104a-d may comprise at least one retraction element 106. Preferably, each fingerlike blade 104a-d may comprise one, two, three, or more retraction elements 106a-c. In some embodiments, the retraction elements 106a-c may be along the curvature of the fingerlike blades 104a-d. In some embodiments, one of the retraction elements 106c may be positioned at the tip of the fingerlike blade 104a-d. In such an embodiment, the tip has a radius of curvature R1 of approximately 0.04 inch to approximately 0.06 inch. In one example, the radius of curvature R1 of the tip is 0.0534 inch.

The fingerlike blades may have a radius of curvature R2 ranging from approximately 0.1 inch to approximately 0.4 inch. Preferably, the radius of curvature R2 ranges from approximately 0.15 inch to approximately 0.35 inch. In one example, the radius of curvature R2 is 0.1735 inch. In another example the radius of curvature R2 is 0.1810 inch. In another example, the radius of curvature R2 is 0.3187 inch. In another example, the radius of curvature R2 is 0.3112 inch.

In some embodiments, the fingerlike blades 104a-d may have two radii of curvature R2, R3. The first radius of curvature R2 may be where the blade first begins to curve. The second radius of curvature R3 may be towards the tip where the retraction elements 106 are located. Preferably, the first radius of curvature R2 is smaller than the second radius of curvature R3. In one example, the first radius of curvature R2 is 0.1810 inch and the second radius of curvature R3 is 0.3187 inch. In another example, the first radius of curvature R2 is 0.1735 inch and the second radius of curvature R3 is 0.318 inch.

In another embodiment as shown in FIGS. 18A-E, the recurved conical tooth is applied to the Army Navy surgical retractor. The Army Navy surgical retractor has a bend near the tip with a radius of curvature R4 ranging from about 0.3 inch to about 0.5 inch. Preferably, the radius of curvature R4 is 0.4 inch. In one example, the retraction elements 106 have an anteroposterior tip distance 402 of approximately 0.1750 inch, a lateral tip distance 400 of approximately 0.1200 inch, and a height H1 of approximately 0.0650 inch.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A surgical retractor, comprising:
   a. a handle;
   b. a blade operatively connected to the handle via a neck; and
   c. a plurality of retraction elements projecting from the blade,
   wherein the retraction elements are configured to minimize tearing of a glove during use without compromising gripping action against tissue,
   wherein each retraction element comprises a base, a back wall, an anterior side, a first sidewall, and a second sidewall,
   wherein the base and the back wall define a posterior edge, the back wall and the first sidewall define a first dorsolateral edge, the back wall and the second sidewall define a second dorsolateral edge, the base and the first sidewall define a first ventrolateral edge, and the base and the second sidewall define a second ventrolateral edge,
wherein the back wall, the anterior side, the first sidewall, and the second sidewall of each retraction element converge at a curved tip, and
wherein each curved tip is defined by an anteroposterior radius of curvature and a lateral radius of curvature, where the anteroposterior radius of curvature is different than the lateral radius of curvature.

2. The surgical retractor of claim 1,
wherein the anteroposterior radius of curvature ranges from approximately 0.01 inch to approximately 0.025 inch.

3. The surgical retractor of claim 2,
wherein the lateral radius of curvature ranges from approximately 0.02 inch to approximately 0.035 inch.

4. The surgical retractor of claim 1,
wherein the anterior side of each retraction element is curved having a radius of curvature of the anterior side of approximately 0.030 inch to approximately 0.08 inch.

5. The surgical retractor of claim 4,
wherein the back wall of each retraction element is curved having a radius of curvature of the back wall of approximately 0.05 inch to approximately 0.15 inch.

6. The surgical retractor of claim 1,
wherein the base of each retraction element has a width of approximately 0.06 inch to approximately 0.10 inch.

7. The surgical retractor of claim 1,
wherein a length of each retraction element is approximately 0.05 inch to approximately 0.10 inch.

8. The surgical retractor of claim 1,
wherein each retraction element has a height of approximately 0.05 inch to approximately 0.075 inch.

9. The surgical retractor of claim 1,
wherein the retraction elements are spaced apart so as to define a lateral distance between each curved tip of approximately 0.08 inch to approximately 0.25 inch.

10. The surgical retractor of claim 9,
wherein the retraction elements are spaced apart so as to define an anteroposterior distance between each curved tip of approximately 0.10 inch to approximately 0.20 inch.

11. The surgical retractor of claim 1,
wherein each of the retraction elements comprises an oblique pyramid.

12. The surgical retractor of claim 1,
wherein the retraction elements are configured to be locked in an exposed or deployed configuration.

13. The surgical retractor of claim 1,
wherein the blade comprises a flexible blade such that flexion of the blade causes the retraction elements to deploy.

14. The surgical retractor of claim 13,
wherein the tips of the retraction elements are exposed when the retraction elements are deployed.

15. The surgical retractor of claim 1,
wherein the retraction elements comprise retraction elements that are integrally formed as a single unit.

16. The surgical retractor of claim 1,
further comprising a slide bracket wherein the slide bracket is slidably attached to the neck.

17. The surgical retractor of claim 1,
wherein the retraction elements are folded in a stowed position to prevent the retraction elements from catching tissue or a glove.

18. The surgical retractor of claim 1,
further comprising a lock to lock the blade in a deployed position.

19. The surgical retractor of claim 1,
wherein the blade comprises a concave surface, a convex surface, an attached end and a free end that is opposite the attached end.

20. A surgical retractor, comprising:
a handle;
a blade operatively connected to the handle via a neck; and
a plurality of retraction elements projecting from the blade,
wherein the retraction elements are configured to minimize tearing of a glove during use without compromising gripping action against tissue,
wherein each retraction element comprises a base, a back wall, an anterior side, a first sidewall, and a second sidewall,
wherein the base and the back wall define a posterior edge, the back wall and the first sidewall define a first dorsolateral edge, the back wall and the second sidewall define a second dorsolateral edge, the base and the first sidewall define a first ventrolateral edge, and the base and the second sidewall define a second ventrolateral edge,
wherein the back wall, the anterior side, the first sidewall, and the second sidewall of each retraction element converge at a curved tip,
wherein each curved tip comprises an anteroposterior radius of curvature and a lateral radius of curvature, and
wherein the anterior side of each retraction element is curved having a radius of curvature that is less than the radius of curvature of the back wall of each retraction element.

21. A surgical retractor, comprising:
a handle;
a blade operatively connected to the handle via a neck; and
a plurality of retraction elements projecting from the blade,
wherein the retraction elements are configured to minimize tearing of a glove during use without compromising gripping action against tissue,
wherein each retraction element comprises a base, a back wall, an anterior side, a first sidewall, and a second sidewall,
wherein the base and the back wall define a posterior edge, the back wall and the first sidewall define a first dorsolateral edge, the back wall and the second sidewall define a second dorsolateral edge, the base and the first sidewall define a first ventrolateral edge, and the base and the second sidewall define a second ventrolateral edge,
wherein the back wall, the anterior side, the first sidewall, and the second sidewall of each retraction element converge at a curved tip,
wherein each curved tip is defined by an anteroposterior radius of curvature and a lateral radius of curvature, where the anteroposterior radius of curvature is different than the lateral radius of curvature, and
wherein the anterior side of each retraction element is curved having a radius of curvature that is less than the radius of curvature of the back wall of each retraction element.

* * * * *